(12) United States Patent
Djupesland et al.

(10) Patent No.: US 10,639,437 B2
(45) Date of Patent: May 5, 2020

(54) DELIVERY DEVICES

(71) Applicants: Per Gisle Djupesland, Oslo (NO);
Rune Harald Gaarder, Oslo (NO);
Sébastien Lamolle, Oslo (NO)

(72) Inventors: Per Gisle Djupesland, Oslo (NO);
Rune Harald Gaarder, Oslo (NO);
Sébastien Lamolle, Oslo (NO)

(73) Assignee: OptiNose AS, Oslo (NO)

( * ) Notice: Subject to any disclaimer, the term of this patent is extended or adjusted under 35 U.S.C. 154(b) by 566 days.

(21) Appl. No.: 14/694,300

(22) Filed: Apr. 23, 2015

(65) Prior Publication Data

US 2016/0074603 A1 Mar. 17, 2016

Related U.S. Application Data

(63) Continuation of application No. 12/516,399, filed as application No. PCT/IB2007/004355 on Nov. 28, 2007, now Pat. No. 9,038,630.

(30) Foreign Application Priority Data

Nov. 28, 2006 (GB) .................................. 0623728.3

(51) Int. Cl.
*A61M 15/08* (2006.01)
*A61M 15/00* (2006.01)

(52) U.S. Cl.
CPC .... *A61M 15/0098* (2014.02); *A61M 15/0021* (2014.02); *A61M 15/0023* (2014.02);
(Continued)

(58) Field of Classification Search
CPC ........ A61M 11/00; A61M 11/001-008; A61M 11/02-08; A61M 13/00; A61M 15/06;
(Continued)

(56) References Cited

U.S. PATENT DOCUMENTS

| | | | |
|---|---|---|---|
| 419,942 A * | 1/1890 | Harding | ................... 128/203.15 |
| 605,436 A | 6/1898 | Kellogg | |

(Continued)

FOREIGN PATENT DOCUMENTS

| | | |
|---|---|---|
| GB | 2246299 | 1/1992 |
| GB | 2349092 | 10/2000 |

(Continued)

OTHER PUBLICATIONS

Cindy H. Dubin, *Nothing to Sneeze At*, Pharmaceutical Formulation & Quality Magazine (Jan. 29, 2003).
(Continued)

*Primary Examiner* — Michael J Tsai
*Assistant Examiner* — Ned T Heffner
(74) *Attorney, Agent, or Firm* — Finnegan, Henderson, Farabow, Garrett & Dunner LLP

(57) ABSTRACT

A delivery device for and method of delivering a metered amount of substance, the delivery device comprising: a mouthpiece through which a user in use exhales; an outlet through which substance is in use delivered; a housing fluidly connected to the mouthpiece and the outlet, such that exhalation by the user through the mouthpiece creates an air flow through the housing and from the outlet; and a substance-dispensing unit which is disposed within the housing and operative to dispense a metered amount of substance into an entraining air flow as created through the housing.

9 Claims, 22 Drawing Sheets

(52) U.S. Cl.
CPC .... *A61M 15/0028* (2013.01); *A61M 15/0035* (2014.02); *A61M 15/0041* (2014.02); *A61M 15/08* (2013.01); *A61M 2202/04* (2013.01); *A61M 2202/064* (2013.01); *A61M 2205/073* (2013.01); *A61M 2206/16* (2013.01)

(58) Field of Classification Search
CPC ................ A61M 15/08; A61M 15/085; A61M 15/0028; A61M 15/0065–0078; A61M 15/0085; A61M 15/009
See application file for complete search history.

(56) References Cited

U.S. PATENT DOCUMENTS

| | | | |
|---|---|---|---|
| 642,748 | A | 2/1900 | Manners |
| 658,436 | A | 9/1900 | Groth |
| 746,749 | A | 12/1903 | Seidel |
| 902,832 | A | 11/1908 | Philbrook |
| 1,375,325 | A | 4/1921 | Schaefer |
| 5,645,050 | A | 7/1997 | Zierenberg et al. |
| 5,647,347 | A | 7/1997 | Van Oort |
| 5,797,392 | A | 8/1998 | Keldmann et al. |
| 6,648,848 | B1 | 11/2003 | Keldmann et al. |
| 6,715,485 | B1* | 4/2004 | Djupesland ......... A61M 3/0279 128/203.12 |
| D530,815 | S | 10/2006 | Murphy et al. |
| 7,347,201 | B2 | 3/2008 | Djupesland |
| 7,377,901 | B2 | 5/2008 | Djupesland et al. |
| 7,481,218 | B2 | 1/2009 | Djupesland |
| 7,543,581 | B2 | 6/2009 | Djupesland |
| 7,740,014 | B2 | 6/2010 | Djupesland |
| 7,784,460 | B2 | 8/2010 | Djupesland et al. |
| 7,841,337 | B2 | 11/2010 | Djupesland |
| 7,854,227 | B2 | 12/2010 | Djupesland |
| 7,934,503 | B2 | 5/2011 | Djupesland et al. |
| 7,975,690 | B2 | 6/2011 | Djupesland |
| 8,047,202 | B2 | 11/2011 | Djupesland |
| 8,146,589 | B2 | 4/2012 | Djupesland |
| 8,171,929 | B2 | 5/2012 | Djupesland et al. |
| 8,327,844 | B2 | 12/2012 | Djupesland |
| 8,511,303 | B2 | 8/2013 | Djupesland |
| 8,522,778 | B2 | 9/2013 | Djupesland |
| 8,550,073 | B2 | 10/2013 | Djupesland |
| 8,555,877 | B2 | 10/2013 | Djupesland |
| 8,555,878 | B2 | 10/2013 | Djupesland |
| 8,590,530 | B2 | 11/2013 | Djupesland et al. |
| 8,596,278 | B2 | 12/2013 | Djupesland |
| 8,800,555 | B2 | 8/2014 | Djupesland |
| 8,875,704 | B2 | 11/2014 | Djupesland et al. |
| 8,899,229 | B2 | 12/2014 | Djupesland et al. |
| 8,910,629 | B2 | 12/2014 | Djupesland et al. |
| D723,156 | S | 2/2015 | Djupesland et al. |
| D725,769 | S | 3/2015 | Djupesland et al. |
| 8,978,647 | B2 | 3/2015 | Djupesland et al. |
| 9,010,325 | B2 | 4/2015 | Djupesland et al. |
| 9,038,630 | B2 | 5/2015 | Djupesland et al. |
| 9,067,034 | B2 | 6/2015 | Djupesland et al. |
| 9,072,857 | B2 | 7/2015 | Djupesland |
| 9,108,015 | B2 | 8/2015 | Djupesland |
| 9,119,932 | B2 | 9/2015 | Djupesland |
| 9,132,249 | B2 | 9/2015 | Djupesland |
| 9,144,652 | B2 | 9/2015 | Djupesland et al. |
| 9,168,341 | B2 | 10/2015 | Djupesland |
| 9,205,208 | B2 | 12/2015 | Djupesland |
| 9,205,209 | B2 | 12/2015 | Djupesland |
| 9,272,104 | B2 | 3/2016 | Djupesland |
| D759,805 | S | 6/2016 | Djupesland |
| D761,951 | S | 7/2016 | Djupesland |
| 9,452,272 | B2 | 9/2016 | Djupesland et al. |
| 9,468,727 | B2 | 10/2016 | Djupesland |
| D773,644 | S | 12/2016 | Djupesland |
| 2004/0024330 | A1 | 2/2004 | Djupesland et al. |
| 2004/0112378 | A1 | 6/2004 | Djupesland |
| 2004/0112379 | A1 | 6/2004 | Djupesland |
| 2004/0112380 | A1 | 6/2004 | Djupesland |
| 2004/0149289 | A1 | 8/2004 | Djupesland |
| 2004/0182388 | A1 | 9/2004 | Djupesland |
| 2005/0028812 | A1 | 2/2005 | Djupesland |
| 2005/0072430 | A1 | 4/2005 | Djupesland |
| 2005/0235992 | A1 | 10/2005 | Djupesland |
| 2006/0096589 | A1 | 5/2006 | Djupesland |
| 2006/0107957 | A1 | 5/2006 | Djupesland |
| 2006/0169278 | A1 | 8/2006 | Djupesland et al. |
| 2006/0180148 | A1 | 8/2006 | Beller |
| 2006/0219240 | A1 | 10/2006 | Djupesland |
| 2006/0219241 | A1 | 10/2006 | Djupesland |
| 2006/0225732 | A1 | 10/2006 | Djupesland |
| 2006/0231094 | A1 | 10/2006 | Djupesland |
| 2007/0039614 | A1 | 2/2007 | Djupesland |
| 2007/0125371 | A1 | 6/2007 | Djupesland |
| 2007/0186927 | A1 | 8/2007 | Djupesland et al. |
| 2008/0161771 | A1 | 7/2008 | Djupesland |
| 2008/0163874 | A1 | 7/2008 | Djupesland |
| 2008/0221471 | A1 | 9/2008 | Djupesland et al. |
| 2008/0223363 | A1 | 9/2008 | Djupesland |
| 2008/0289629 | A1* | 11/2008 | Djupesland ....... A61M 15/0028 128/203.15 |
| 2009/0101146 | A1 | 4/2009 | Djupesland |
| 2009/0293873 | A1 | 12/2009 | Djupesland et al. |
| 2009/0304802 | A1 | 12/2009 | Djupesland et al. |
| 2009/0314293 | A1 | 12/2009 | Djupesland |
| 2009/0320832 | A1 | 12/2009 | Djupesland |
| 2010/0035805 | A1 | 2/2010 | Hafner |
| 2010/0051022 | A1 | 3/2010 | Djupesland et al. |
| 2010/0057047 | A1 | 3/2010 | Djupesland et al. |
| 2010/0242959 | A1 | 9/2010 | Djupesland et al. |
| 2010/0282246 | A1 | 11/2010 | Djupesland et al. |
| 2010/0288275 | A1 | 11/2010 | Djupesland et al. |
| 2010/0300439 | A1 | 12/2010 | Djupesland et al. |
| 2011/0023869 | A1 | 2/2011 | Djupesland |
| 2011/0053827 | A1 | 3/2011 | Hafner |
| 2011/0088690 | A1 | 4/2011 | Djupesland et al. |
| 2011/0088691 | A1 | 4/2011 | Djupesland |
| 2011/0114087 | A1 | 5/2011 | Djupesland et al. |
| 2011/0126830 | A1 | 6/2011 | Djupesland et al. |
| 2011/0259329 | A1 | 10/2011 | Djupesland et al. |
| 2011/0318345 | A1 | 12/2011 | Djupesland |
| 2012/0000459 | A1 | 1/2012 | Djupesland |
| 2012/0006323 | A1 | 1/2012 | Djupesland |
| 2012/0073571 | A1 | 3/2012 | Djupesland |
| 2012/0090608 | A1 | 4/2012 | Djupesland et al. |
| 2012/0260915 | A1 | 10/2012 | Djupesland |
| 2013/0098362 | A1 | 4/2013 | Djupesland et al. |
| 2013/0125889 | A1 | 5/2013 | Djupesland et al. |
| 2013/0327320 | A1 | 12/2013 | Djupesland |
| 2014/0018295 | A1 | 1/2014 | Djupesland |
| 2014/0041660 | A1 | 2/2014 | Djupesland et al. |
| 2014/0060536 | A1 | 3/2014 | Djupesland |
| 2014/0073562 | A1 | 3/2014 | Djupesland |
| 2014/0144442 | A1 | 5/2014 | Djupesland et al. |
| 2014/0144443 | A1 | 5/2014 | Djupesland et al. |
| 2014/0166008 | A1 | 6/2014 | Djupesland |
| 2014/0202456 | A1 | 7/2014 | Djupesland |
| 2014/0246022 | A1 | 9/2014 | Djupesland et al. |
| 2015/0007811 | A1 | 1/2015 | Djupesland et al. |
| 2015/0013670 | A1 | 1/2015 | Djupesland et al. |
| 2015/0013677 | A1 | 1/2015 | Djupesland et al. |
| 2015/0053201 | A1 | 2/2015 | Djupesland et al. |
| 2015/0090259 | A1 | 4/2015 | Djupesland et al. |
| 2015/0101605 | A1 | 4/2015 | Djupesland et al. |
| 2015/0144129 | A1 | 5/2015 | Djupesland et al. |
| 2015/0165139 | A1 | 6/2015 | Hafner |
| 2015/0182709 | A1 | 7/2015 | Djupesland |
| 2015/0246194 | A1 | 9/2015 | Djupesland et al. |
| 2015/0367090 | A1 | 12/2015 | Djupesland et al. |
| 2015/0367091 | A1 | 12/2015 | Djupesland et al. |
| 2016/0001022 | A1 | 1/2016 | Djupesland et al. |
| 2016/0045687 | A1 | 2/2016 | Djupesland |
| 2016/0051778 | A1 | 2/2016 | Djupesland et al. |
| 2016/0074603 | A1 | 3/2016 | Djupesland et al. |
| 2016/0082206 | A1 | 3/2016 | Djupesland et al. |
| 2016/0082207 | A1 | 3/2016 | Djupesland et al. |
| 2016/0166788 | A1 | 6/2016 | Djupesland et al. |

(56) References Cited

U.S. PATENT DOCUMENTS

| | | | |
|---|---|---|---|
| 2016/0184537 A1 | 6/2016 | Djupesland | |
| 2016/0193435 A1 | 7/2016 | Djupesland | |
| 2016/0250408 A1 | 9/2016 | Djupesland | |
| 2016/0263334 A1 | 9/2016 | Djupesland | |
| 2016/0279357 A1 | 9/2016 | Djupesland | |
| 2016/0310683 A1 | 10/2016 | Djupesland et al. | |
| 2016/0331916 A1 | 11/2016 | Djupesland et al. | |

FOREIGN PATENT DOCUMENTS

| | | |
|---|---|---|
| GB | 2404867 | 2/2005 |
| GB | 2405350 | 3/2005 |
| GB | 2418147 | 3/2006 |
| GB | 2424587 | 10/2006 |
| GB | 2440316 | 1/2008 |
| WO | WO 95/11715 | 5/1995 |
| WO | WO 96/22802 | 8/1996 |
| WO | WO 98/53869 | 12/1998 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/060458 | 7/2004 |
| WO | WO 2004/103447 | 12/2004 |
| WO | WO 2005/016423 | 2/2005 |
| WO | WO 2005/021059 | 3/2005 |
| WO | WO 2005/028006 | 3/2005 |
| WO | WO 2006/030210 | 3/2006 |
| WO | WO 2006/090149 | 8/2006 |
| WO | WO 2007/001650 | 1/2007 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vlckovia et al., *Effective Treatment of Mild-to-Moderate Nasal Polyposis with Fluticasone Delivered by a Novel Device*, Rhinology (Oct. 22, 2009).
Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).
P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).
F.S. Hansen et al., *Preliminary Efficacy of Fluticasone Delivered by a Novel Device in Recalcitrant Chronic Rhinosinusitis*, Rhinology (Jun. 26, 2010).
Per Gisle Djupesland, *Nasal Drug Delivery Devices: Characteristics and Performance in Clinical Perspective—A Review*, Drug. Deliv. And Transl. Res. (Oct. 18, 2012).
Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).
Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

(56) References Cited

OTHER PUBLICATIONS

R. Mahmoud, *Breathe Out,* Innovations in Phar, Tech. (Dec. 10, 2015).

* cited by examiner

DELIVERY DEVICES

This is a continuation application of U.S. application Ser. No. 12/516,399, filed May 21, 2010, which is the national stage entry of PTC/IB07/04355, which claims priority to GB 0623728.3 filed on Nov. 28, 2006 each of which are incorporated herein by reference.

The present invention relates to a delivery device for and method of delivering a metered amount of substance, in particular a delivery device for delivering a metered dose of particulate substance to a nasal cavity of a subject.

Many delivery devices exist for the delivery of powdered substances, such as disclosed in the applicant's earlier WO-A-2000/051672.

Whilst these delivery devices have found extensive application, the present inventors have recognized the need for a delivery device which utilizes the exhalation breath of a user as the driving force to deliver a metered dose of powdered substance, and in particular which is of low cost, such as to allow for use in high-volume applications, typically in the delivery of vaccines.

The present inventors have also recognized the need for a compact device, which in one embodiment allows for manual actuation, thus allowing for operation in emergency situations, such as when the subject is unconscious.

In one aspect the present invention provides a delivery device for delivering a metered amount of substance, the delivery device comprising: a mouthpiece through which a user in use exhales; an outlet through which substance is in use delivered; a housing fluidly connected to the mouthpiece and the outlet, such that exhalation by the user through the mouthpiece creates an air flow through the housing and from the outlet; and a substance-dispensing unit which is disposed within the housing and operative to dispense a metered amount of substance into an entraining air flow as created through the housing.

In one embodiment the substance-dispensing unit includes a baffle member which separates the housing, such as to define an inlet cavity which is upstream of the baffle member and an outlet cavity which is downstream of the baffle member, and supports a container for containing substance which includes an opening which in use opens to the outlet cavity, with the baffle member including at least one entraining air flow channel which is disposed adjacent the container and provides a fluid communication path between the inlet and outlet cavities, such as to provide for delivery of at least one entraining air flow adjacent the opening of the container which entrains substance when dispersed from the container, and a dispersion member which provides for delivery of at least one dispersing air flow into the container to disperse the substance from the container and into the at least one entraining air flow as generated through the at least one entraining air flow channel.

In one embodiment the baffle member includes a plurality of entraining air flow channels which are disposed about the periphery of the container.

In one embodiment the entraining air flow channels are arranged on an annulus surrounding the container.

In one embodiment the entraining air flow channels are arranged symmetrically.

In one embodiment the entraining air flow channels are configured to provide substantially parallel air flows.

In another embodiment the entraining air flow channels are configured to provide converging air flows which converge at a location over the opening to the container.

In one embodiment the dispersion member includes at least one dispersion air flow channel which is configured to provide for at least one dispersing air flow into the container in a direction opposite the at least one entraining air flow.

In one embodiment the at least one dispersion air flow channel provides for delivery of at least one dispersing air flow at an angle inclined in a vertical orient relative to the opening of the container.

In one embodiment the at least one dispersion air flow channel provides for delivery of the at least one dispersing air flow with a tangential component in a horizontal orient relative to the opening of the container.

In one embodiment the dispersion member includes first and second dispersion air flow channels.

In one embodiment the first and second dispersion air flow channels are disposed to opposite sides of the container.

In one embodiment the first and second dispersion flow channels are non-symmetrically arranged.

In one embodiment the first and second dispersion air flow channels are configured to provide for dispersing air flows which are inclined at different angles in a vertical orient relative to the opening of the container.

In one embodiment the substance-dispensing unit includes a sleeve member which is disposed in the outlet cavity, such as to define a delivery chamber through which the at least one entraining air flow is in use delivered to the outlet.

In one embodiment the sleeve member further defines a reservoir chamber which is fluidly connected to the inlet cavity and the at least one dispersion air flow channel.

In one embodiment the reservoir chamber is an annular chamber which surrounds at least in part the delivery chamber.

In one embodiment the outlet is a nosepiece and the delivery device is a nasal delivery device for delivering substance to the nasal airway of the user.

In one embodiment the substance particulate substance, and preferably a powdered substance.

In another aspect the present invention provides a delivery device for delivering a metered amount of substance, the delivery device comprising: a mouthpiece through which a user in use exhales; an outlet unit through which substance is in use delivered; a housing including a cavity which includes an inlet fluidly connected to the mouthpiece and an outlet fluidly connected to the outlet unit; a piston member which is slideably disposed within the cavity; and a rupturable membrane which normally fluidly separates the outlet unit from the cavity and defines a gas chamber containing a volume of gas between the piston member and the rupturable membrane; wherein the piston member is slideably disposed in the cavity under bias of a driving pressure created with exhalation by the user into the mouthpiece, such that, on exhalation by the user, the piston member is driven forwardly to reduce the volume of the gas chamber and thereby provide for compression of the gas contained in the gas chamber, and, following a predeterminable compression of the gas chamber, the rupturable membrane is ruptured, providing for delivery of a gas flow entraining substance through the outlet unit.

In one embodiment the cavity is an elongate cavity.

In one embodiment the piston member includes a rupturing element which acts to rupture the rupturable membrane following displacement of the piston member by a predeterminable distance.

In another embodiment the rupturable membrane is configured to rupture at a predeterminable pressure.

In one embodiment the delivery device further comprises: an enclosed compressible member which is disposed forwardly of the piston member and compressed by movement of the piston member, wherein the compressible member defines the gas chamber and provides the rupturable membrane at a forward end thereof.

In one embodiment the substance is contained in the gas chamber.

In another embodiment the delivery device further comprises: a further rupturable membrane which together with the first-mentioned rupturable membrane defines a substance-containing chamber containing substance forwardly of the gas chamber, wherein the further rupturable membrane is configured to rupture following rupturing of the first-mentioned rupturable membrane, whereby a gas flow delivered from the gas chamber entrains the substance contained in the substance-containing chamber.

In one embodiment the outlet unit is a nosepiece and the delivery device is a nasal delivery device for delivering substance to the nasal airway of the user.

In one embodiment the substance is a particulate substance, and preferably a powdered substance.

In a further aspect the present invention provides a delivery device for delivering a metered amount of substance, the delivery device comprising: a mouthpiece through which a user in use exhales; an outlet unit through which substance is in use delivered; a housing including a first, piston cavity which includes an inlet fluidly connected to the mouthpiece, a second, substance-containing cavity for containing a metered amount of substance which includes an inlet and an outlet fluidly connected to the outlet unit, and a by-pass channel which includes an inlet fluidly connected to the piston cavity at a location along a length thereof and an outlet fluidly connected to the inlet of the substance-containing cavity; a piston member which is slideably disposed within the piston cavity; and a rupturable membrane which normally fluidly separates the outlet unit from the substance containing cavity; wherein the piston member is slideably disposed in the piston cavity under bias of a driving pressure created with exhalation by the user into the mouthpiece, such that, on exhalation by the user, the piston member is driven forwardly, causing rupturing of the rupturable membrane, and, following displacement of the piston member forwardly of the inlet of the by-pass channel, an exhalation air flow is delivered through the by-pass channel and the substance-containing cavity, thereby providing for delivery of a gas flow entraining substance through the outlet unit.

In one embodiment the cavity is an elongate cavity.

In one embodiment the piston member includes a rupturing element which acts to rupture the rupturable membrane following displacement of the piston member by a predeterminable distance.

In another embodiment the rupturable membrane is configured to rupture at a predeterminable pressure.

In one embodiment the outlet unit is a nosepiece and the delivery device is a nasal delivery device for delivering substance to the nasal airway of the user.

In one embodiment the substance is a particulate substance, and preferably a powdered substance.

In a still further aspect the present invention provides a delivery device for delivering a metered amount of substance, the delivery device comprising: a mouthpiece unit through which a user can in use exhale; an outlet unit through which substance is in use delivered; a substance-supply unit which is actuatable to deliver substance; and a body unit in which the substance-supply unit Is movably disposed between a storage configuration and an operative configuration, in which the substance-supply unit is actuatable; wherein the mouthpiece unit is coupled to the substance supply unit, such that the substance-supply unit is moved between the storage and operative configurations by the mouthpiece unit.

In one embodiment the outlet unit is integrally formed with the body unit.

In one embodiment the mouthpiece unit is at least partially contained within the body unit when the substance-supply unit is in the storage configuration, and withdrawn from the body unit when the substance supply unit is in the operative configuration.

In one embodiment the body unit comprises a housing which includes a cavity in which the substance-supply unit is slideably disposed.

In one embodiment the mouthpiece unit is articulated to the substance-supply unit, such as to allow the mouthpiece unit to be folded relative to the outlet unit when the substance-supply unit is in the operative configuration, thereby enabling positioning of the mouthpiece and outlet units to an operative configuration.

In one embodiment the mouthpiece unit is fluidly connected to the substance-supply unit, such as to provide for actuation of the substance-supply unit in response to exhalation by the user through the mouthpiece unit.

In one embodiment the mouthpiece unit and the substance-supply unit are configured such that the mouthpiece unit can act as a plunger manually to actuate the substance-supply unit, without requiring generation of an exhalation air flow to actuate the substance-supply unit.

In one embodiment the outlet unit is a nosepiece and the delivery device is a nasal delivery device for delivering substance to the nasal airway of the user.

In one embodiment the substance is a particulate substance, and preferably a powdered substance.

In another embodiment the substance is a liquid substance.

In a yet further aspect the present invention provides a delivery device for delivering a metered amount of substance, the delivery device comprising: a mouthpiece unit through which a user can in use exhale; an outlet unit through which substance is in use delivered; a substance-supply unit which is actuatable to deliver substance; and a body unit in which the mouthpiece unit is movably disposed between a storage configuration in which the mouthpiece unit is at least partially contained within the body unit and an operative configuration in which the mouthpiece unit is extended from the body unit.

In one embodiment the outlet unit is integrally formed with the body unit.

In one embodiment the body unit comprises a housing which includes a cavity in which the mouthpiece unit is slicleably disposed.

In one embodiment the mouthpiece unit is articulated to the substance-supply unit, such as to allow the mouthpiece unit to be folded relative to the outlet unit when the mouthpiece unit is in the operative configuration, thereby enabling positioning of the mouthpiece and outlet units to an operative configuration.

In one embodiment the mouthpiece unit is fluidly connected to the substance-supply unit, such as to provide for actuation of the substance-supply unit in response to exhalation by the user through the mouthpiece unit.

In one embodiment the mouthpiece unit and the substance-supply unit are configured such that the mouthpiece unit can act as a plunger manually to actuate the substance-supply unit, without requiring generation of an exhalation air flow to actuate the substance-supply unit.

In one embodiment the outlet unit is a nosepiece and the delivery device is a nasal delivery device for delivering substance to the nasal airway of the user.

In one embodiment the substance is a particulate substance, and preferably a powdered substance.

In another embodiment the substance is a liquid substance.

Preferred embodiments of the present invention will now be described hereinbelow by way of example only with reference to the accompanying drawings, in which.

Figure 18:
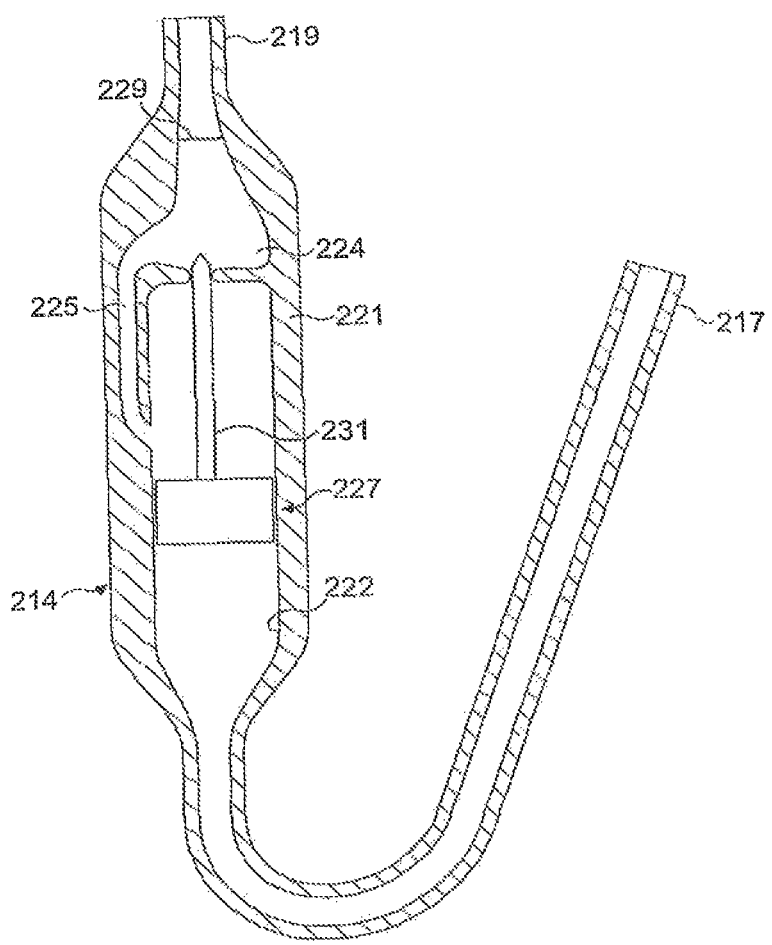
FIG. 18 illustrates a sectional view of a delivery device in accordance with a sixth embodiment of the present invention, where in an inoperative or rest state.
Figure 19:
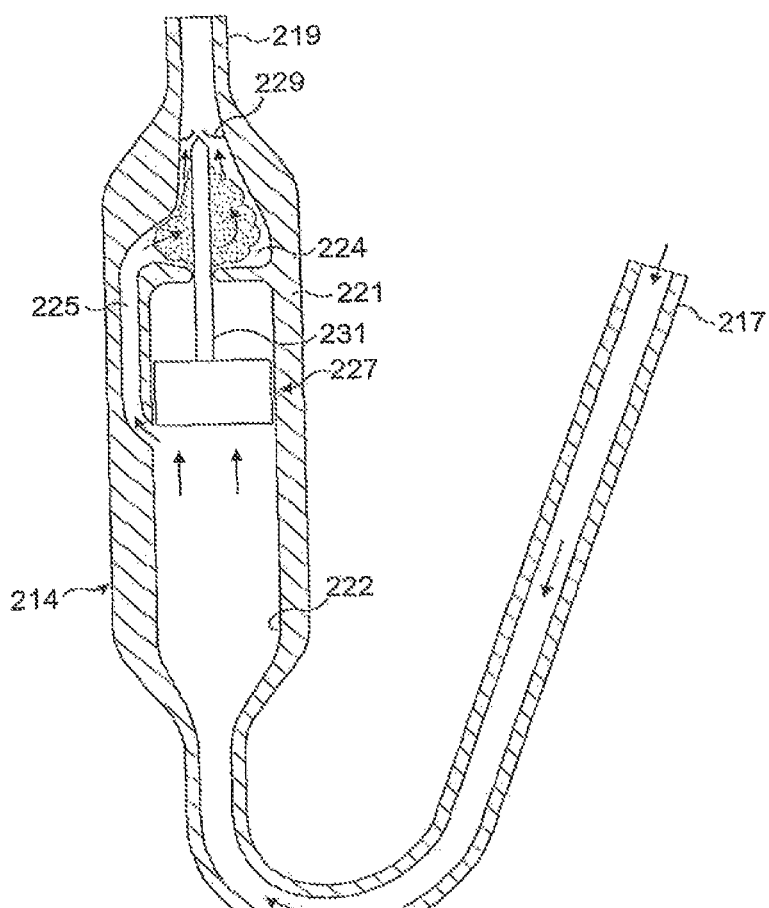
Figure 20:
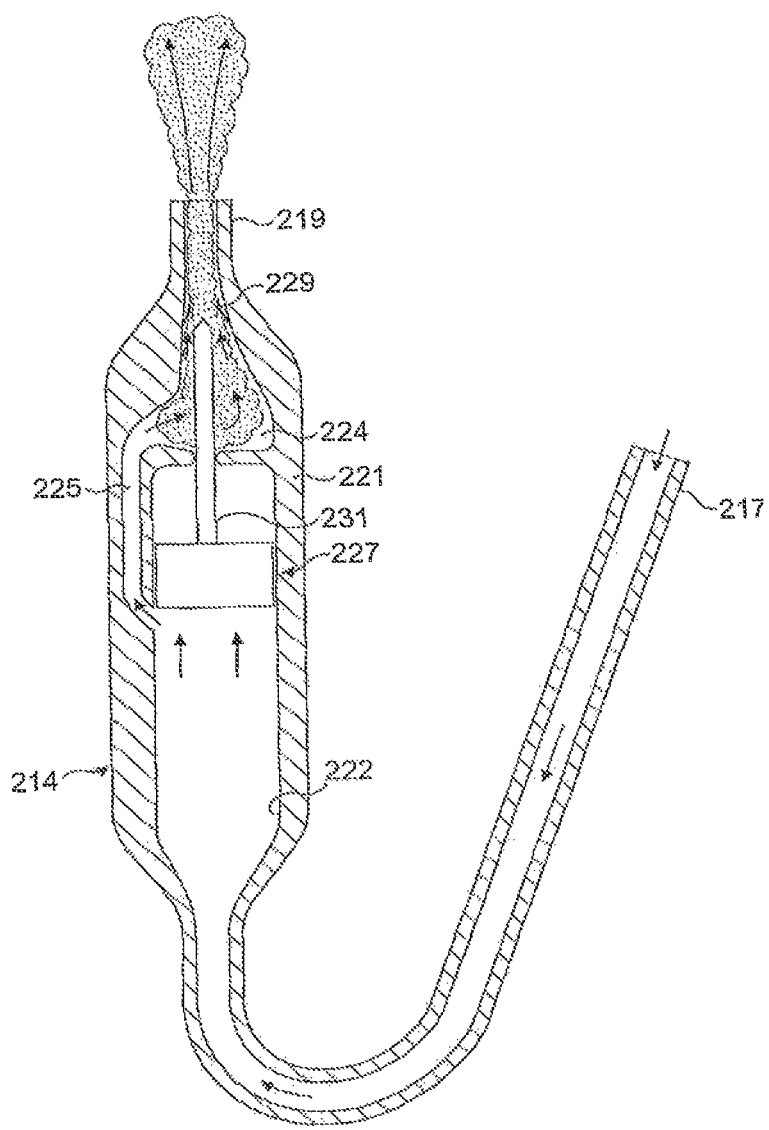
Figure 21:
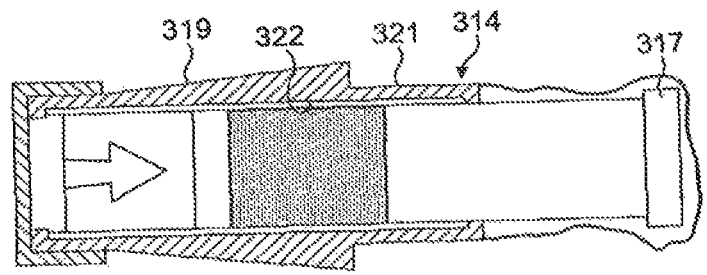
Figure 22:
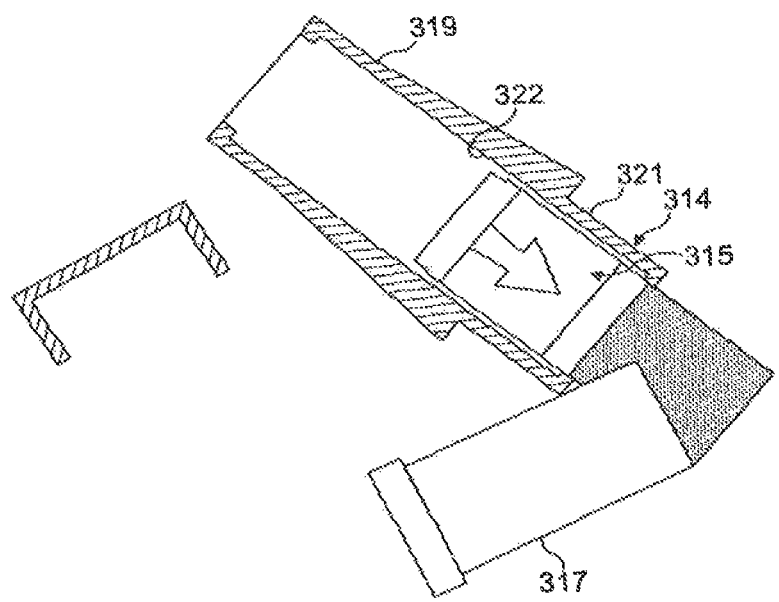
Figure 23:
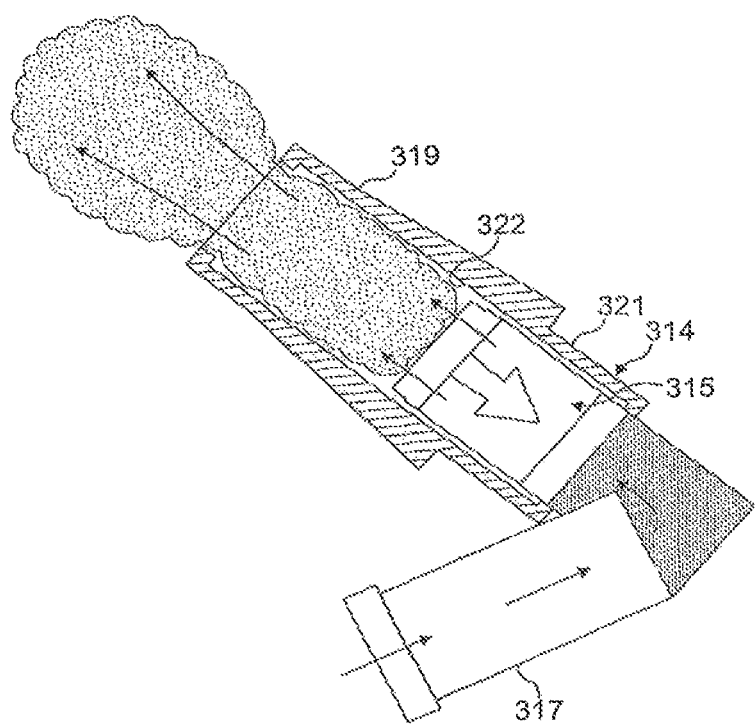
Figure 24:
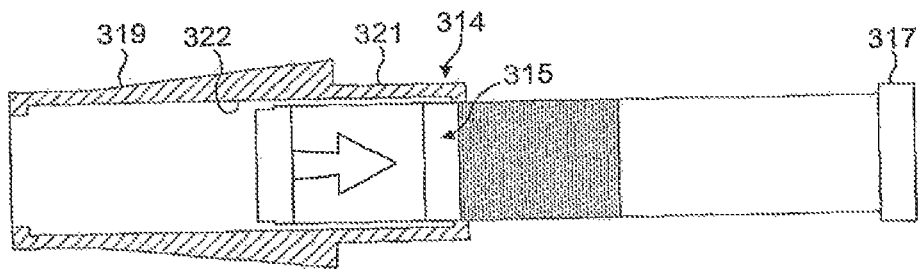
Figure 25:
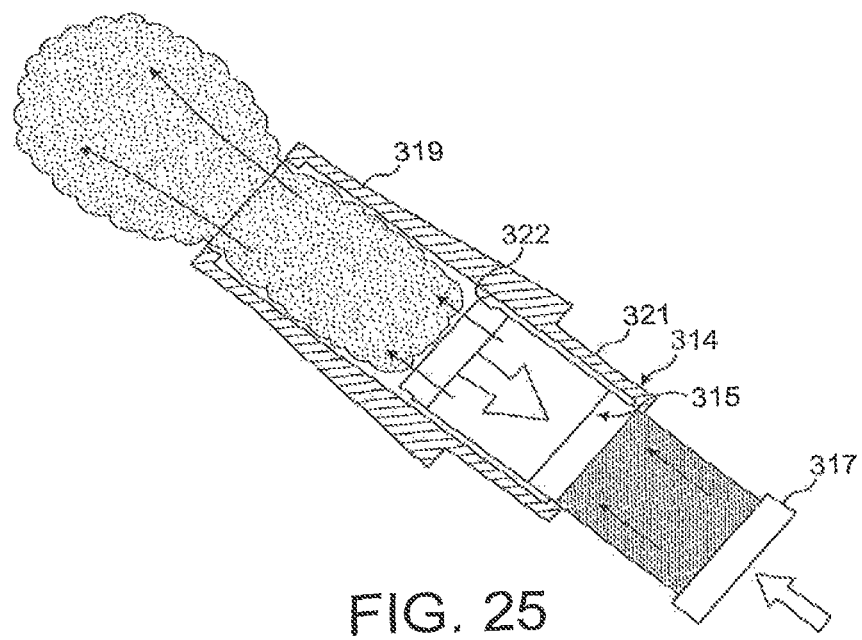

FIG. 19 illustrates a sectional view of the delivery device of FIG. 18, where in a first operative state in which a user has exhaled sufficiently to drive the piston member to rupture the rupturable membrane; and FIG. 20 illustrates a sectional view of the delivery device of FIG. 18, where in a second operative state in which an air flow entraining powdered substance is delivered by the delivery device;

FIG. 21 illustrates a sectional view of a delivery device in accordance with a seventh embodiment of the present invention, where in an inoperative or rest state;

FIG. 22 illustrates the delivery device of FIG. 21 in one, normal operative configuration, prior to actuation of the delivery device;

FIG. 23 illustrates the delivery device of FIG. 21, where in the normal operative configuration, following actuation of the delivery device;

FIG. 24 illustrates the delivery device of FIG. 21 in another operative configuration, prior to actuation of the delivery device; and FIG. 25 illustrates the delivery device of FIG. 21, where in the other operative configuration, following actuation of the delivery device.

Figure 1:
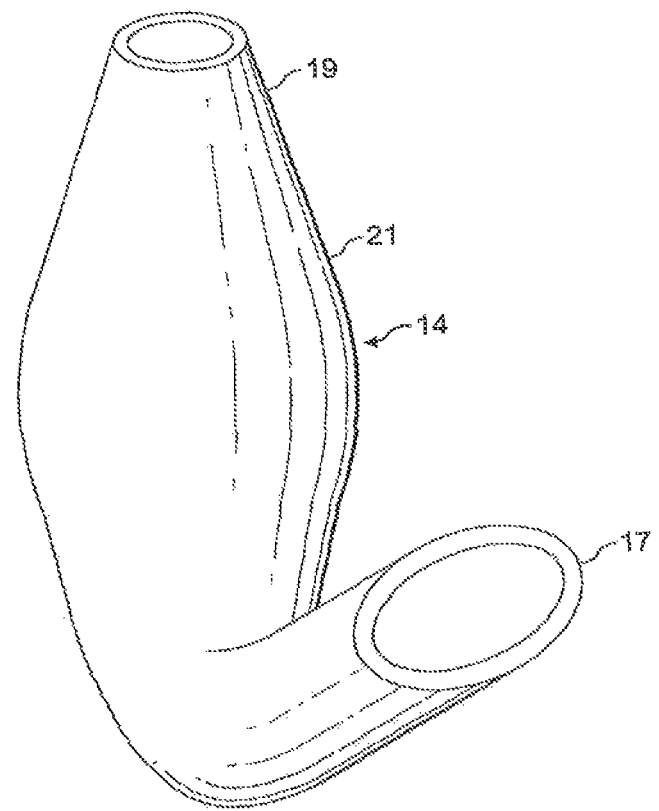
FIG. 1 illustrates a perspective view of a delivery device in accordance with a first embodiment of the present invention.
Figure 2:
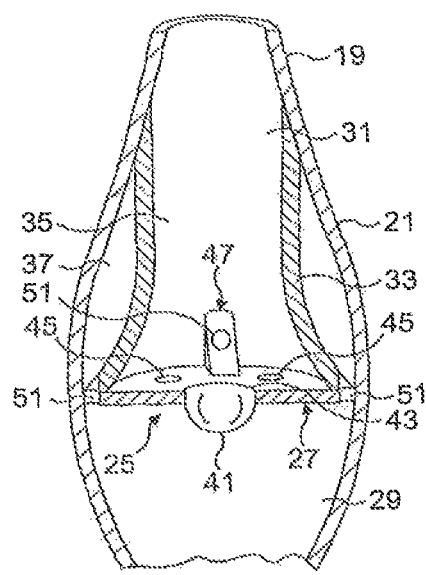
FIG. 2 illustrates a fragmentary, perspective sectional view of the delivery device of FIG. 1, where in an inoperative or rest state.
Figure 3:
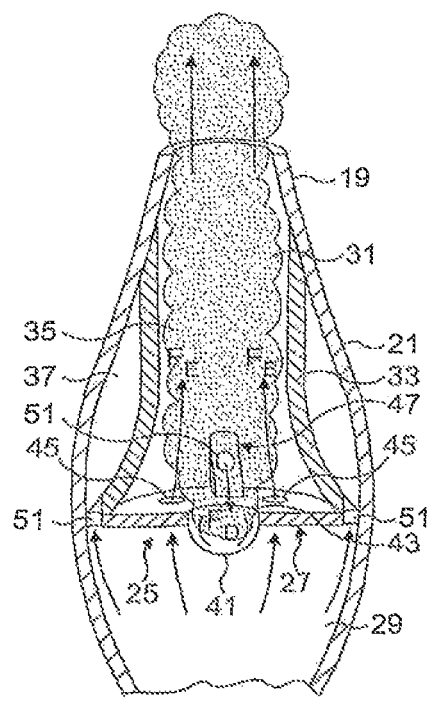
FIG. 3 illustrates a fragmentary, perspective sectional view of the delivery device of FIG. 1, where in an operative state.

FIGS. 1 to 3 illustrate a delivery device in accordance with a first embodiment of the present invention.

The delivery device comprises a body unit 14, which is typically gripped in the hand of a user, a mouthpiece 17 through which the user exhales, and a nosepiece 19 for fitting to a nostril of the user and through which substance, in this embodiment particulate substance, here a powdered substance, is delivered to the nasal airway of the user.

In this embodiment the mouthpiece 17 and the nosepiece 19 are integrally formed with the body unit 14, but in other embodiments the mouthpiece 17 and the nosepiece 19 could be formed separately of the body unit 14.

The body unit 14 comprises a housing 21, in this embodiment a tubular section, one, inlet end of which is fluidly connected to the mouthpiece 17 and the other, outlet end of which is fluidly connected to the nosepiece 19, and a substance dispensing unit 25 which is disposed within the housing 21 and provides for dispensing of a metered amount of powdered substance into an entraining air flow as delivered through the housing 21, in this embodiment as achieved by exhalation through the mouthpiece 17, as will be described in more detail hereinbelow.

The substance dispensing unit 25 comprises a baffle member 27 which extends across the housing 21, such as to define an inlet cavity 29 which is upstream of the baffle member 27 and an outlet cavity 31 which is downstream of the baffle member 27, a sleeve member 33 which is disposed in the outlet cavity 31, such as to define a first, delivery chamber 35, in this embodiment within the sleeve member 33, through which an entraining air flow entraining powdered substance is in use delivered and a second, air chamber 37, in this embodiment a substantially annular chamber between the sleeve member 33 and the housing 21, which provides an air reservoir, the purpose of which will be described in more detail hereinbelow, and a substance-containing container 41, in this embodiment a blister element, which is disposed to the baffle member 27, in this embodiment on the longitudinal axis of the housing 21, and includes an opening 43 which opens into the delivery chamber 35.

The baffle member 27 includes at least one, in this embodiment a plurality of first flow channels 45 which are disposed about the periphery of the container 41 and provide a fluid communication path between the inlet cavity 29 and the delivery chamber 35, such as to provide for delivery of an entraining air flow adjacent the periphery of the container 41 which acts to entrain the powdered substance as dispersed from the container 41.

In this embodiment the first flow channels 45, here four in number, are arranged symmetrically on an annulus located about the periphery of the container 41.

In this embodiment the first flow channels 45 have a diameter of from about 1 mm to about 2 mm, preferably from about 1.2 mm to about 1.7 mm. In one embodiment the first flow channels 45 have a diameter of about 1.2 mm. In another embodiment the first flow channels 45 have a diameter of about 1.7 mm.

In this embodiment the first flow channels 45 are configured to provide for parallel air flows which extend substantially parallel to the longitudinal axis of the delivery chamber 35.

In an alternative embodiment the first flow channels 45 could be configured to provide for converging air flows which converge towards the longitudinal axis of the delivery chamber 35.

The baffle member 27 further includes at least one, in this embodiment a plurality of second flow channels 51 which are disposed about the periphery thereof and provide a fluid communication path between the inlet cavity 29 and the air chamber 37, such as to provide for a reservoir of pressurised air within the air chamber 37 on exhalation by the user through the mouthpiece 17.

The substance dispensing unit 25 further comprises a dispersion member 47 which is configured to provide for delivery of a dispersing air flow into the container 41, such as to disperse the powdered substance from within the container 41 and into the entraining air flow as generated through the first flow channels 45.

In this embodiment the dispersion member 47 includes at least one flow channel 51 which is configured to provide for delivery of at least one dispersing air flow into the container 41 in a direction opposite the entraining air flow as delivered through the delivery chamber 35.

In this embodiment the at least one flow channel 51 provides for delivery of at least one dispersing air flow at an angle inclined in a vertical orient to the opening 43 of the container 41.

In a preferred embodiment the at least one flow channel 51 provides for delivery of the at least one dispersing air flow with a tangential component in a horizontal orient to the opening 43 of the container 41. This configuration advantageously provides for the development of a swirling action to the powdered substance as contained by the container 41, which swirling action acts to promote the emptying of the powdered substance from the container 41 into the entraining air flow as generated through the delivery chamber 35 on exhalation by the user.

In this embodiment the at least one flow channel 51 is fluidly connected to the air chamber 37, such that the at least one dispersing air flow is provided from an air reservoir as created by the exhalation breath of the user.

In this embodiment the dispersion member 47 comprises first and second dispersion flow channels 51 which are disposed to opposite sides of the container 41. In one embodiment the first and second dispersion flow channels 51 are non-symmetrically arranged. In this embodiment the first and second dispersion flow channels 51 are configured to provide for dispersion air flows which are inclined at different angles in the vertical orient relative to the opening 43 of the container 41.

In an alternative embodiment the dispersion member 47 could comprise a single dispersion flow channel 51 which is disposed adjacent the container 41.

Operation of the above-described delivery device will now be described hereinbelow with particular reference to FIG. 3 of the accompanying drawings.

The user first inserts the nosepiece 19 into one of his or her nostrils and grips the mouthpiece 17 in his or her mouth.

The user then exhales through the mouthpiece 17, which provides for the generation of a plurality of entraining air flows $F_E$ through the first flow channels 45 in the baffle member 27, and the development of a pressurised supply of air in the air reservoir as defined by the air chamber 37, which provides for delivery of at least one dispersing air flow $F_D$ from the at least one dispersion flow channel 51 into the container 41.

The delivery of the at least one dispersing air flow $F_D$ into the container 41 acts to disperse the powdered substance from the container 41, which powdered substance is then entrained by the entraining air flow $F_E$ and delivered through the nostril and into the nasal cavity of the user.

In one embodiment the entraining air flow $F_E$ is at such a pressure and flow as to provide for flow around the posterior margin of the nasal septum and out of the other nostril of the user, in the manner as described in the applicant's earner WO-A-2000/051672, the content of which is incorporated herein by reference.

In one alternative embodiment the container 41 could be rotatably disposed to the baffle member 27 such as to be rotated with exhalation through the mouthpiece 17. In one embodiment the container 41 could be configured as a symmetric body which spins substantially about its own axis. In one embodiment the container 41 could be configured as an asymmetric body, such that the container 41 spins in an eccentric manner which acts to promote vibration and delivery of the contained powder.

Figure 4:
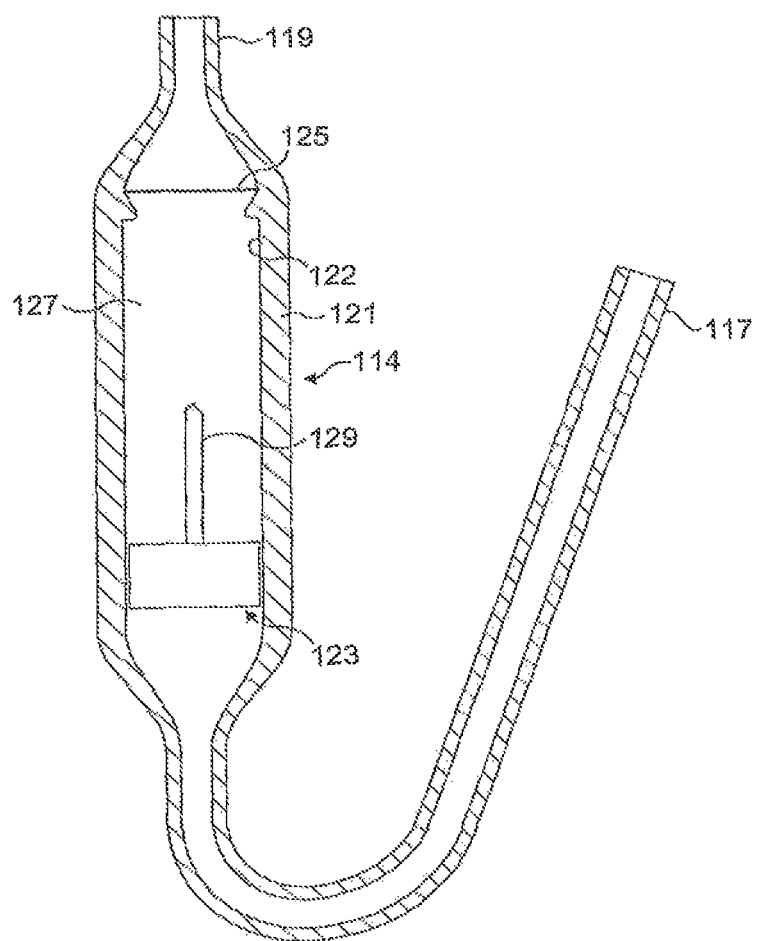
FIG. 4 illustrates a sectional view of a delivery device in accordance with a second embodiment of the present invention, where in an inoperative or rest state.
Figure 5:
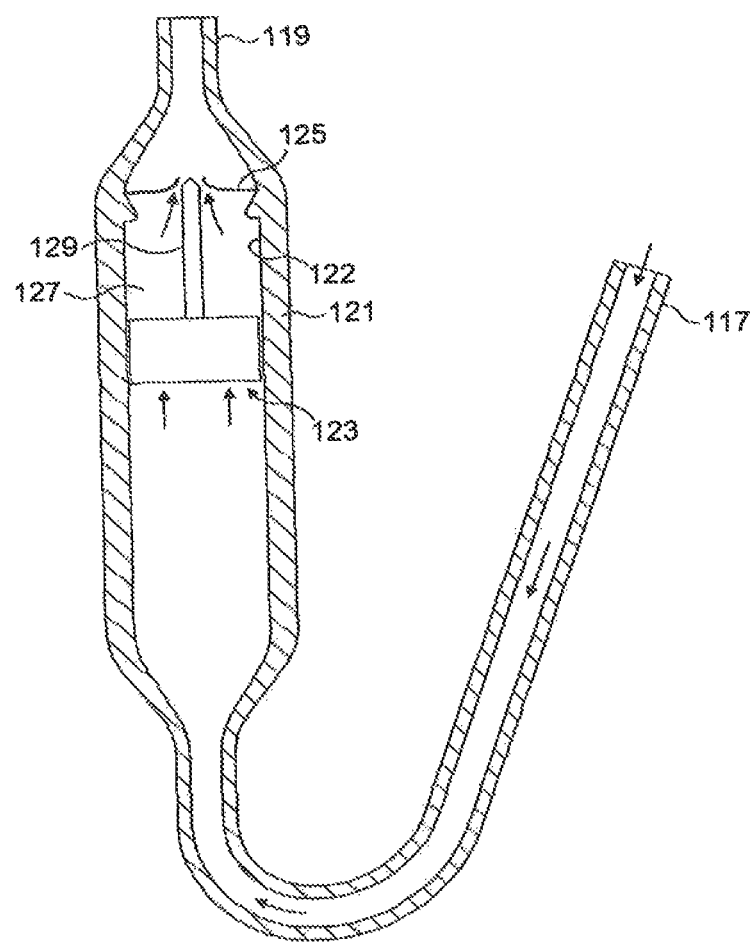
FIG. 5 illustrates a sectional view of the delivery device of FIG. 4, where in a first operative state in which a user has exhaled sufficiently to drive the piston member to rupture the rupturable membrane.
Figure 6:
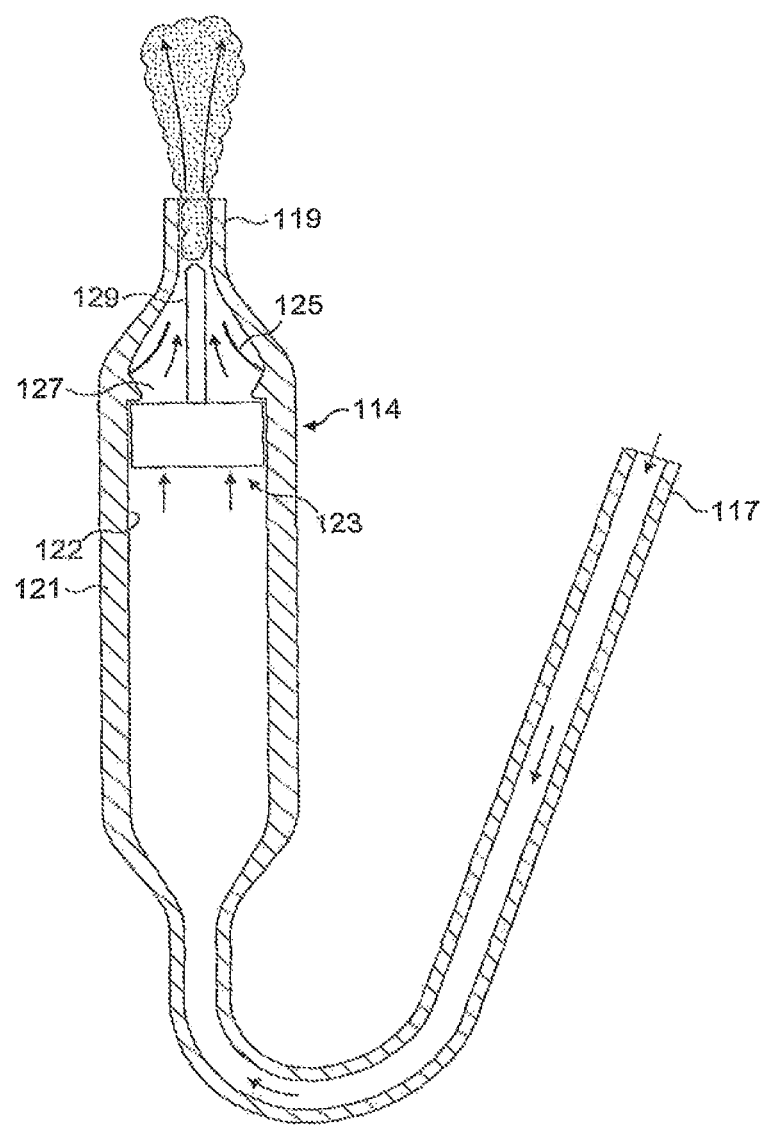
FIG. 6 illustrates a sectional view of the delivery device of FIG. 4, where in a second operative state in which a gas flow entraining powdered substance is delivered by the delivery device.

FIGS. 4 to 6 illustrate a delivery device in accordance with a second embodiment of the present invention.

The delivery device comprises a body unit 114, which is typically gripped in the hand of a user, a mouthpiece 117 through which the user exhales, and a nosepiece 119 for fitting to a nostril of the user and through which substance, in this embodiment particulate substance, here a powdered substance, is delivered to the nasal airway of the user.

In this embodiment the mouthpiece 117 and the nosepiece 119 are integrally formed with the body unit 114, but in other embodiments the mouthpiece 117 and the nosepiece 119 could be formed separately of the body unit 114.

The body unit 114 comprises a housing 121, in this embodiment a tubular section which defines a cavity 122, one, inlet end of which is fluidly connected to the mouthpiece 117 and the other, outlet end of which is fluidly connected to the nosepiece 119, a piston member 123 which is slideably disposed in sealing engagement within the cavity 122, and a rupturable membrane 125 which is disposed at one, forward end of the cavity 122 and normally fluidly separates the nosepiece 119 from the cavity 122, such as to define an enclosed substance-containing chamber 127 between the piston member 123 and the rupturable membrane 125 which contains a metered amount of powdered substance.

The piston member 123 includes a rupturing element 129 at a forward surface thereof, and is slideably disposed in the cavity 122 in the housing 121 under the bias of the pressure as generated with exhalation by the user into the mouthpiece 117, such that, on exhalation by the user, the piston member 123 is driven forwardly such as to reduce the volume of the chamber 127 and thereby provide for compression of the gas as contained in the chamber 127, and, on displacement of the piston member 123 by a predetermined distance, which provides for compression of the gas as contained in the chamber 127 to a predetermined pressure, the membrane 125 is ruptured, which provides for delivery of a gas flow, which entrains the powdered substance, through the nosepiece 119.

Operation of the above-described delivery device will now be described hereinbelow with particular reference to FIGS. 5 and 6 of the accompanying drawings.

The user first inserts the nosepiece 119 into one of his or her nostrils and grips the mouthpiece 117 in his or her mouth.

The user then exhales through the mouthpiece 117, which provides for the piston member 123 to be driven forwardly under the generated pressure, which is such as to reduce the volume of the chamber 127 and compress the gas as contained in the chamber 127.

As illustrated in FIG. 5, on displacement of the piston member 123 by a predetermined distance, which provides for compression of the gas as contained in the chamber 127 to a predetermined pressure, the membrane 125 is ruptured by the rupturing element 129 of the piston member 123.

As illustrated in FIG. 6, on rupturing the membrane 125, the compressed gas as contained therein is delivered as a gas flow, which entrains the powdered substance and delivers the same through the nosepiece 119 and into the nasal airway of the user.

In one alternative embodiment the rupturing element 129 could be omitted from the piston member 123 and the rupturable membrane 125 could be configured to be ruptured at a predetermined pressure.

In one embodiment the gas flow is at such a pressure and flow as to provide for flow around the posterior margin of the nasal septum and out of the other nostril of the user, in the manner as described in the applicant's earlier WO-A-2000/051672, the content of which is incorporated herein by reference.

Figure 7:
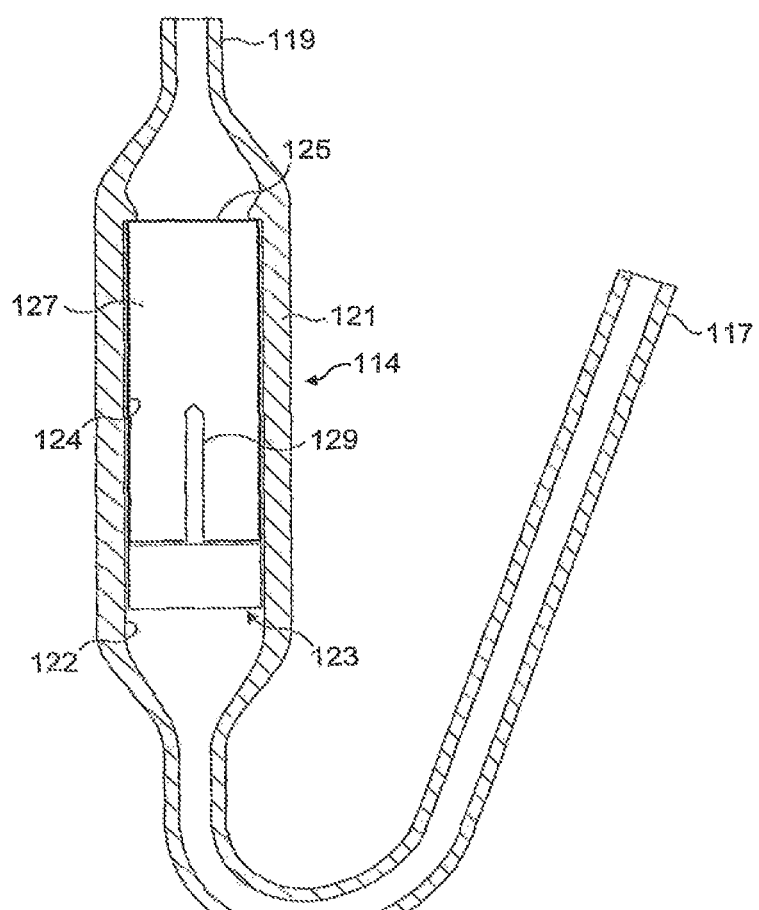
FIG. 7 illustrates a sectional view of a delivery device in accordance with a third embodiment of the present invention, where in an inoperative or rest state.
Figure 8:
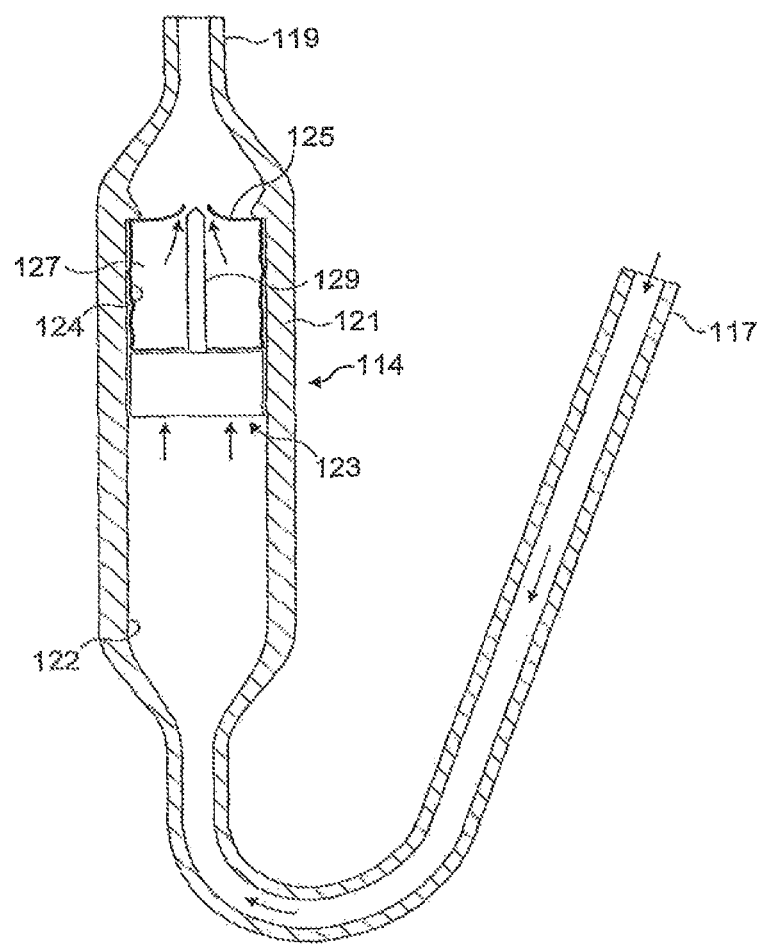
FIG. 8 illustrates a sectional view of the delivery device of FIG. 7, where in a first operative state in which a user has exhaled sufficiently to drive the piston member to rupture the rupturable membrane.
Figure 9:
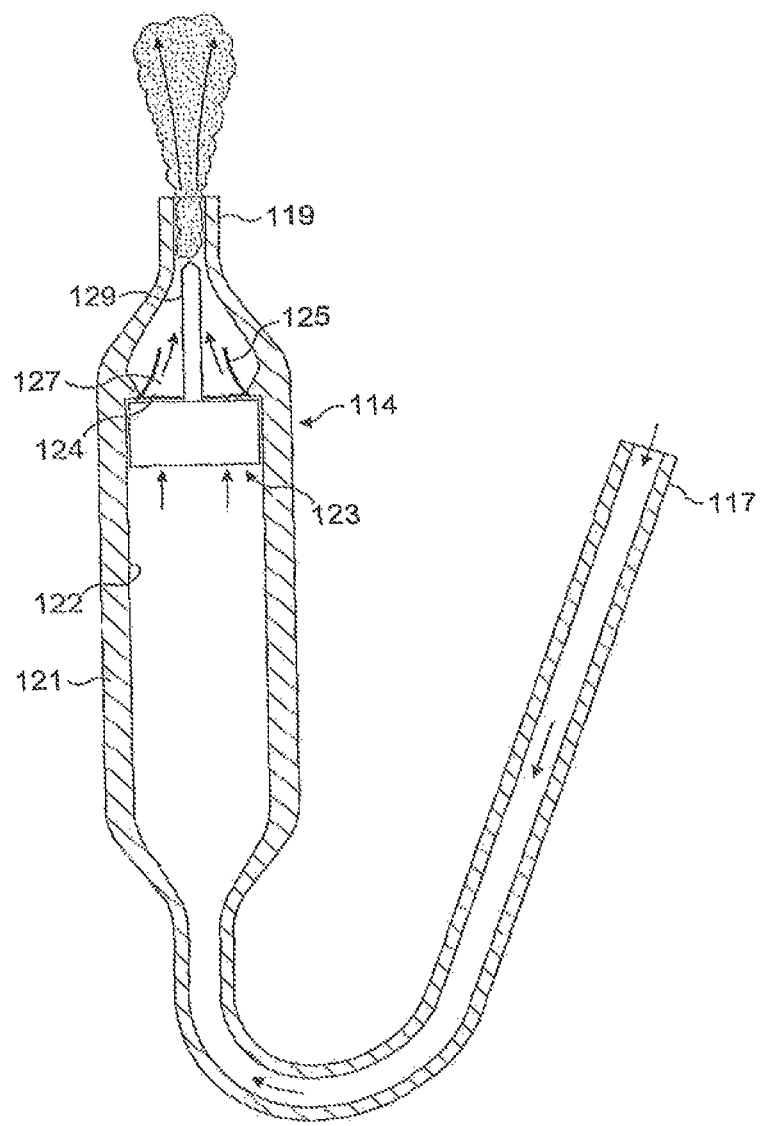
FIG. 9 illustrates a sectional view of the delivery device of FIG. 7, where in a second operative state in which a gas flow entraining powdered substance is delivered by the delivery device.
Figure 10:
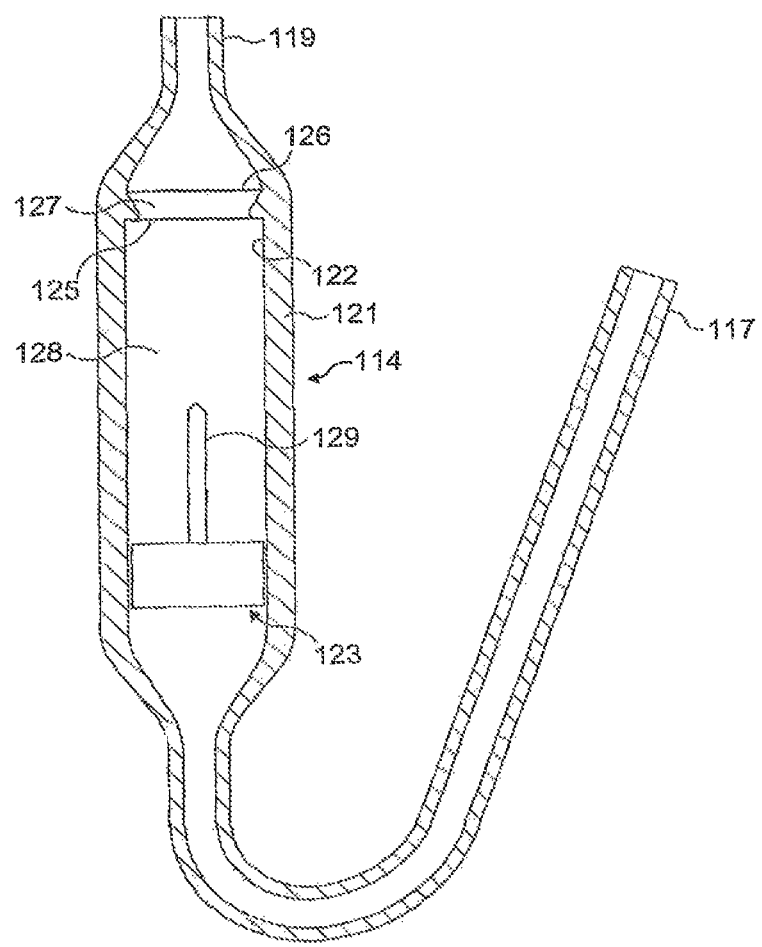
FIG. 10 illustrates a sectional view of a delivery device in accordance with a fourth embodiment of the present invention, where in an inoperative or rest state.

FIGS. 7 to 9 illustrate a delivery device in accordance with a third embodiment of the present invention.

The delivery device comprises a body unit 114, which is typically gripped in the hand of a user, a mouthpiece 117 through which the user exhales, and a nosepiece 119 for fitting to a nostril of the user and through which powdered substance is delivered to the nasal airway of the user.

In this embodiment the mouthpiece 117 and the nosepiece 119 are integrally formed with the body unit 114, but in other embodiments the mouthpiece 117 and the nosepiece 119 could be formed separately of the body unit 114.

The body unit 114 comprises a housing 121, in this embodiment a tubular section which defines a cavity 122, one, inlet end of which is fluidly connected to the mouthpiece 117 and the other, outlet end of which is fluidly connected to the nosepiece 119, a piston member 123 which is slideably disposed within the cavity 122, and an enclosed compressible member 124, in this embodiment of a flexible material, such as a flexible plastics material, which is disposed within the cavity 122 ahead of the piston member 123 and defines a rupturable membrane 125 which is disposed at one, forward end of the cavity 122.

In this embodiment the compressible member 124 defines a substance-containing chamber 127 which contains a metered amount of powdered substance and a volume of gas, which is compressed by displacement of the piston member 123, as will be described in more detail hereinbelow.

In this embodiment the piston member 123 includes a rupturing element 129 at a forward surface thereof, and is slideably disposed in the cavity 122 in the housing 121 under the bias of the pressure as generated with exhalation by the user into the mouthpiece 117, such that, on exhalation by the user, the piston member 123 is driven forwardly such as to compress the compressible member 124 and reduce the volume of the chamber 127, thereby providing for compression of the gas as contained in the chamber 127, and, on displacement of the piston member 123 by a predetermined distance, which provides for compression of the gas as contained in the chamber 127 to a predetermined pressure, the rupturable membrane 125 of the compressible member 124 is ruptured, which provides for the delivery of a gas flow, which entrains the powdered substance, through the nosepiece 119.

Operation of the above-described delivery device will now be described hereinbelow with particular reference to FIGS. 8 and 9 of the accompanying drawings.

The user first inserts the nosepiece 119 into one of his or her nostrils and grips the mouthpiece 117 in his or her mouth.

The user then exhales through the mouthpiece 117, which provides for the piston member 123 to be driven forwardly under the generated pressure, which is such as to compress the compressible member 124 and reduce the volume of the chamber 127, thereby compressing the gas as contained therein.

As illustrated in FIG. 8, on displacement of the piston member 123 by a predetermined distance, which provides for compression of the gas as contained in the chamber 127 to a predetermined pressure, the rupturable membrane 125 is ruptured by the rupturing element 129 of the piston member 123.

As illustrated in FIG. 9, on rupturing the rupturable membrane 125, the compressed gas as contained therein is delivered as a gas flow, which entrains the powdered substance and delivers the same through the nosepiece 119 and into the nasal airway of the user.

In one alternative embodiment the rupturing element 129 could instead be disposed on the body unit 114, such that the rupturable membrane 125 is biased against the rupturing element 129 and ruptured at a predetermined pressure.

In another alternative embodiment the rupturing element 129 could be omitted from the piston member 123 and the rupturable membrane 125 of the compressible member 124 could be configured to be ruptured at a predetermined pressure.

In one embodiment the gas flow is at such a pressure and flow as to provide for flow around the posterior margin of the nasal septum and out of the other nostril of the user, in the manner as described in the applicant's earlier WO-A-2000/051672, the content of which is incorporated herein by reference.

FIGS. 10 to 13 illustrate a delivery device in accordance with a fourth embodiment of the present invention.

The delivery device comprises a body unit 114, which is typically gripped in the hand of a user, a mouthpiece 117 through which the user exhales, and a nosepiece 119 for fitting to a nostril of the user and through which a powdered substance is delivered to the nasal airway of the user.

In this embodiment the mouthpiece 117 and the nosepiece 119 are integrally formed with the body unit 114, but in other embodiments the mouthpiece 117 and the nosepiece 119 could be formed separately of the body unit 114.

The body unit 114 comprises a housing 121, in this embodiment a tubular section which defines a cavity 122, one, inlet end of which is fluidly connected to the mouthpiece 117 and the other, outlet end of which is fluidly connected to the nosepiece 119, a piston member 123 which is slideably disposed in sealing engagement within the cavity 122, and first and second rupturable membranes 125, 126 which are disposed in spaced relation at one, forward end of the cavity 122 and normally fluidly separate the nosepiece 119 from the cavity 122, such as to define an enclosed substance-containing chamber 127 between the rupturable membranes 125, 126 which contains a metered amount of powdered substance and an enclosed compressible gas chamber 128 between the first rupturable membrane 125 and the piston member 123, which contains a volume of gas which is compressed by displacement of the piston member 123, as will be described in more detail hereinbelow.

The piston member 123 includes a rupturing element 129 at a forward surface thereof, and is slideably disposed in the cavity 122 in the housing 121 under the bias of the pressure as generated with exhalation by the user into the mouthpiece 117, such that, on exhalation by the user, the piston member 123 is driven forwardly such as to reduce the volume of the gas chamber 128 and thereby provide for compression of the gas as contained therein, and, on displacement of the piston member 123 by a predetermined distance, which provides for compression of the gas as contained in the gas chamber 128 to a predetermined pressure, the first membrane 125 is ruptured, which provides for delivery of a gas flow to the chamber 127, which entrains the powdered substance as contained therein and causes the second rupturable membrane 126 to be ruptured, such that a gas flow entraining the powdered substance is delivered through the nosepiece 119.

Operation of the above-described delivery device will now be described hereinbelow with particular reference to FIGS. 11 to 13 of the accompanying drawings.

The user first inserts the nosepiece 119 into one of his or her nostrils and grips the mouthpiece 117 in his or her mouth.

The user then exhales through the mouthpiece 117, which provides for the piston member 123 to be driven forwardly under the generated pressure, which is such as to reduce the volume of the gas chamber 128 and compress the gas as contained therein.

Figure 11:
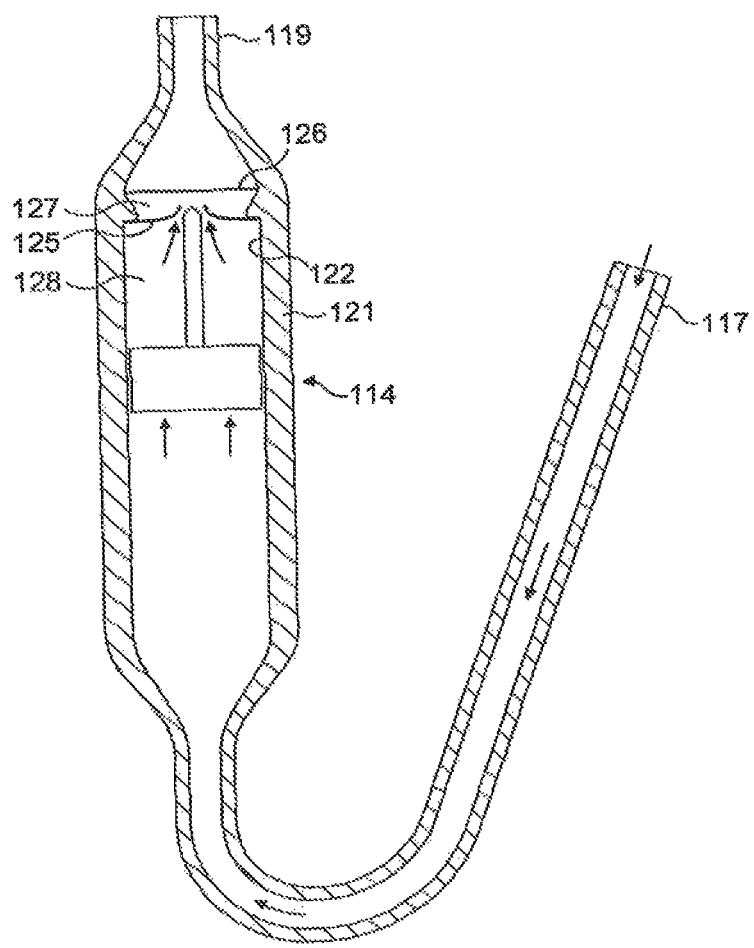
FIG. 11 illustrates a sectional view of the delivery device of FIG. 10, where in a first operative state in which a user has exhaled sufficiently to drive the piston member to rupture the first rupturable membrane.

As illustrated in FIG. 11, on displacement of the piston member 123 by a predetermined distance, which provides for compression of the gas as contained in the gas chamber 128 to a predetermined pressure, the first rupturable membrane 125 is ruptured by the rupturing element 129 of the piston member 123.

On rupturing the first rupturable membrane 125, the compressed gas as contained therein is delivered as a gas flow into the chamber 127, which entrains the powdered substance as contained therein.

Figure 12:
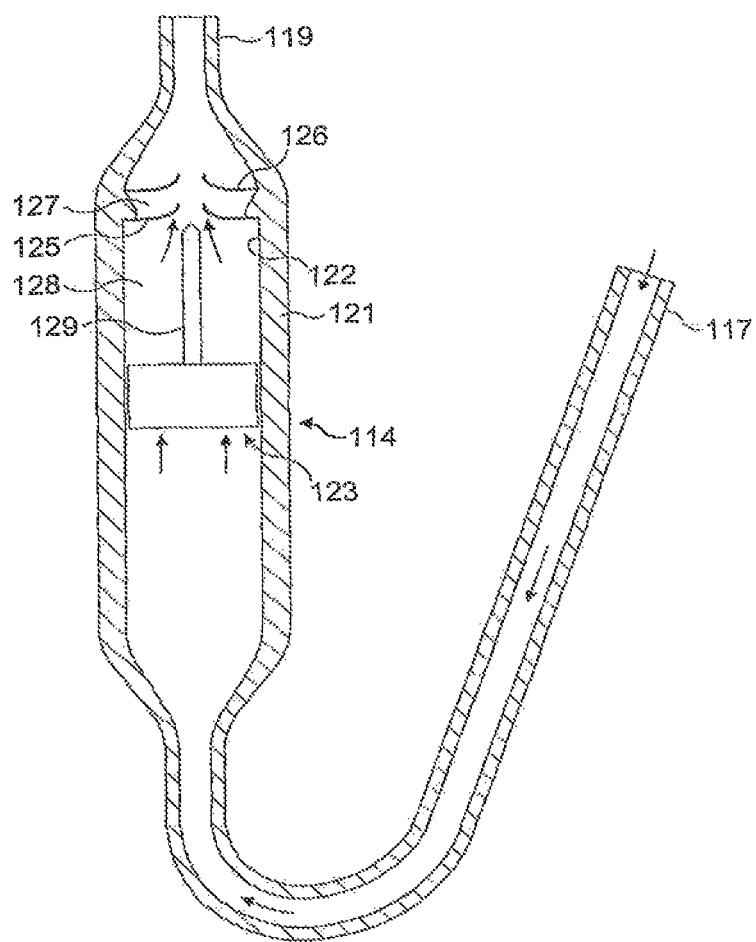
FIG. 12 illustrates a sectional view of the delivery device of FIG. 10, where in a second operative state in which the second rupturable membrane is ruptured by the developed pressure.
Figure 13:
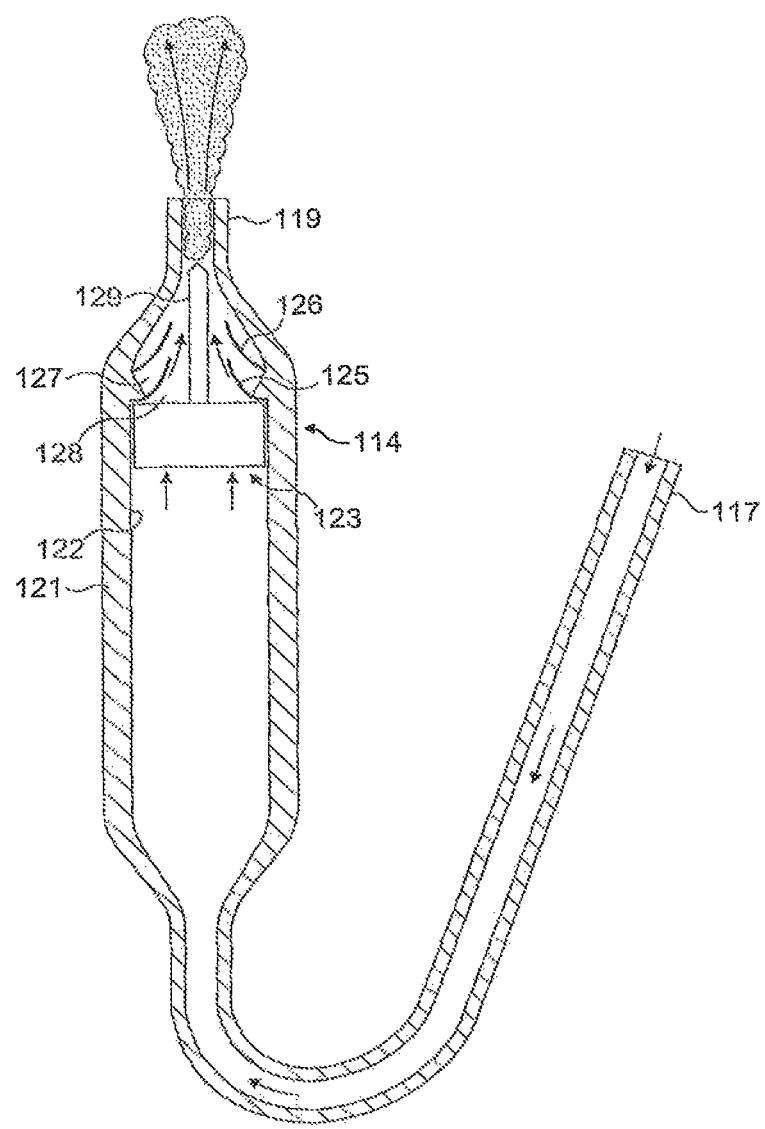
FIG. 13 illustrates a sectional view of the delivery device of FIG. 10, where in a third operative state in which a gas flow entraining powdered substance is delivered by the delivery device.
Figure 14:
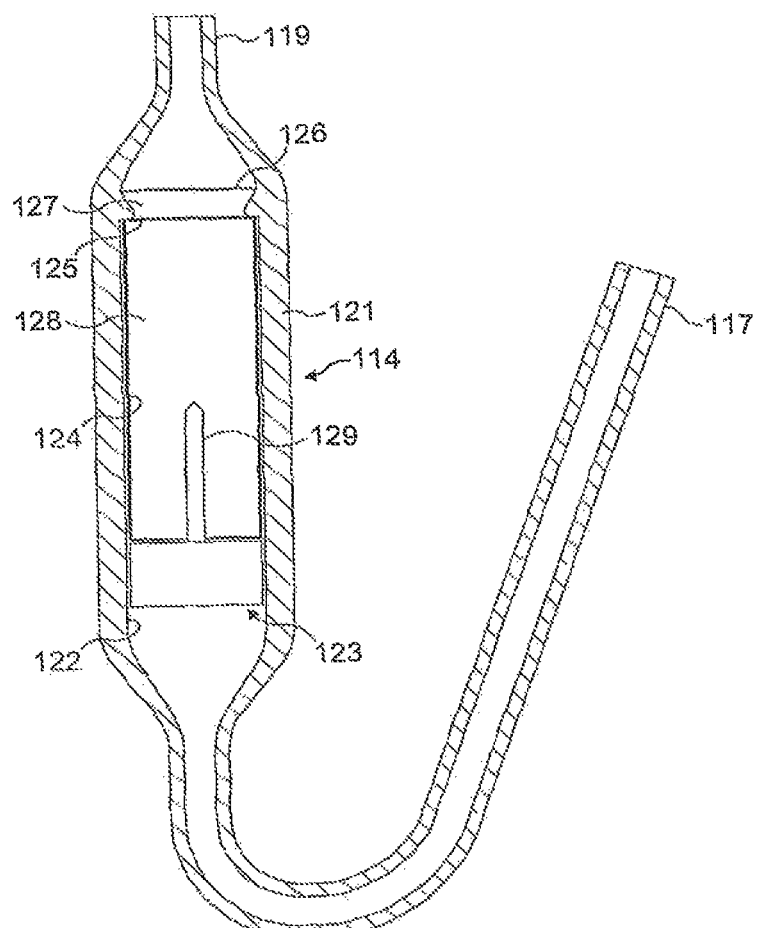
FIG. 14 illustrates a sectional view of a delivery device in accordance with a fifth embodiment of the present invention, where in an inoperative or rest state.

As illustrated in FIG. 12, the delivery of the gas flow into the chamber 127 ruptures the second membrane 126, and, as illustrated in FIG. 13, the gas flow entraining the powdered substance is delivered through the nosepiece 119 and into the nasal airway of the user.

In one alternative embodiment the rupturing element 129 could be omitted from the piston member 123 and the first rupturable membrane 125 of the compressible member 124 could be configured to be ruptured at a predetermined pressure.

In one embodiment the gas flow is at such a pressure and flow as to provide for flow around the posterior margin of the nasal septum and out of the other nostril of the user, in the manner as described in the applicant's earlier WO-A-2000/051672, the content of which is incorporated herein by reference.

FIGS. 14 to 17 illustrate a delivery device in accordance with a fifth embodiment of the present invention.

The delivery device comprises a body unit 114, which is typically gripped in the hand of a user, a mouthpiece 117 through which the user exhales, and a nosepiece 119 for fitting to a nostril of the user and through which substance, in this embodiment particulate substance, here a powdered substance, is delivered to the nasal airway of the user.

In this embodiment the mouthpiece 117 and the nosepiece 119 are integrally formed with the body unit 114, but in other embodiments the mouthpiece 117 and the nosepiece 119 could be formed separately of the body unit 114.

The body unit 114 comprises a housing 121, in this embodiment a tubular section which defines a cavity 122, one, inlet end of which is fluidly connected to the mouthpiece 117 and the other, outlet end of which is fluidly connected to the nosepiece 119, a piston member 123 which is slideably disposed in sealing engagement within the cavity 122, an enclosed compressible member 124, in this embodiment of a flexible material, such as a flexible plastics material, which is disposed within the cavity 122 ahead of the piston member 123 and defines a first rupturable membrane 125 which is disposed at one, forward end of the cavity 122, and a second rupturable membrane 126 which is disposed in spaced relation forwardly from the first rupturable membrane 125 and normally fluidly separates the nosepiece 119 from the cavity 122, such as to define an enclosed substance-containing chamber 127 between the rupturable membranes 125, 126 which contains a metered amount of powdered substance.

In this embodiment the compressible member 124 defines a gas chamber 128 which contains a volume of gas which is compressed by displacement of the piston member 123, as will be described in more detail hereinbelow.

The piston member 123 includes a rupturing element 129 at a forward surface thereof, and is slideably disposed in the cavity 122 in the housing 121 under the bias of the pressure as generated with exhalation by the user into the mouthpiece 117, such that, on exhalation by the user, the piston member 123 is driven forwardly such as to reduce the volume of the gas chamber 128 and provide for compression of the gas as contained therein, and, on displacement of the piston member 123 by a predetermined distance, which provides for compression of the gas as contained in the gas chamber 128 to a predetermined pressure, the first rupturable membrane 125 is ruptured, which provides for delivery of a gas flow to the chamber 127, which entrains the powdered substance as contained therein and causes the second rupturable membrane 126 to be ruptured, such that a gas flow entraining the powdered substance is delivered through the nosepiece 119.

Operation of the above-described delivery device will now be described hereinbelow with particular reference to FIGS. 15 to 17 of the accompanying drawings.

The user first inserts the nosepiece 119 into one of his or her nostrils and grips the mouthpiece 117 in his or her mouth.

The user then exhales through the mouthpiece 117, which provides for the piston member 123 to be driven forwardly under the generated pressure, which is such as to compress the compressible member 124 and reduce the volume of the gas chamber 128, thereby compressing the gas as contained therein.

Figure 15:
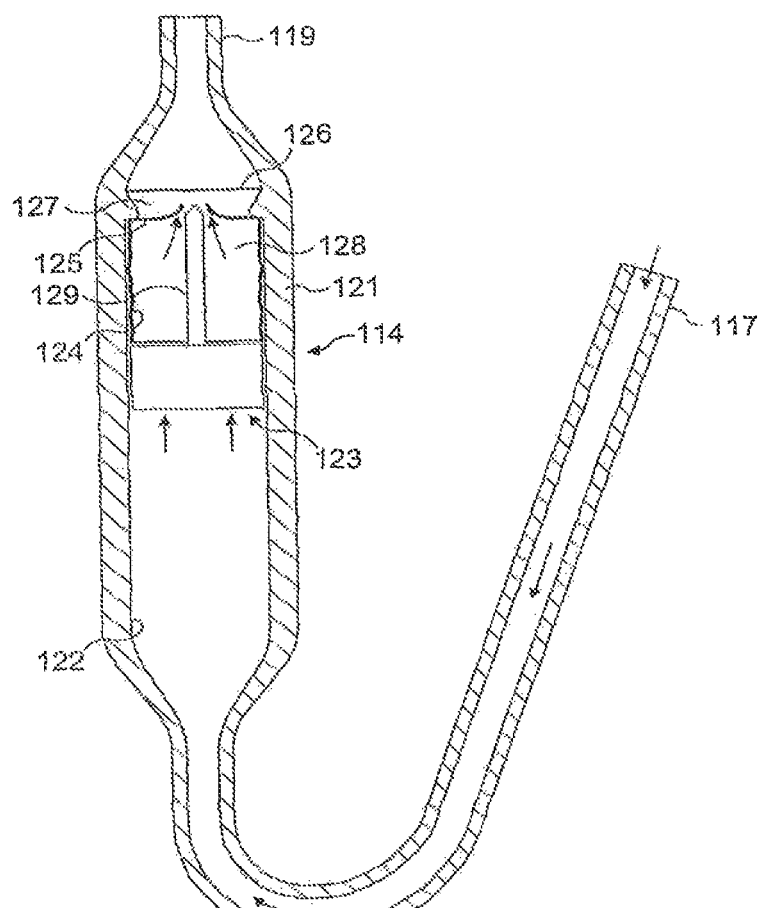
FIG. 15 illustrates a sectional view of the delivery device of FIG. 14, where in a first operative state in which a user has exhaled sufficiently to drive the piston member to rupture the first rupturable membrane.

As illustrated in FIG. 15, on displacement of the piston member 123 by a predetermined distance, which provides for compression of the gas as contained in the gas chamber 128 to a predetermined pressure, the first membrane 125 as defined by the compressible member 124 is ruptured by the rupturing element 129 of the piston member 123.

On rupturing the first membrane 125, the compressed gas as contained in the gas chamber 128 is delivered as a gas flow into the chamber 127, which entrains the powdered substance as contained therein.

Figure 16:
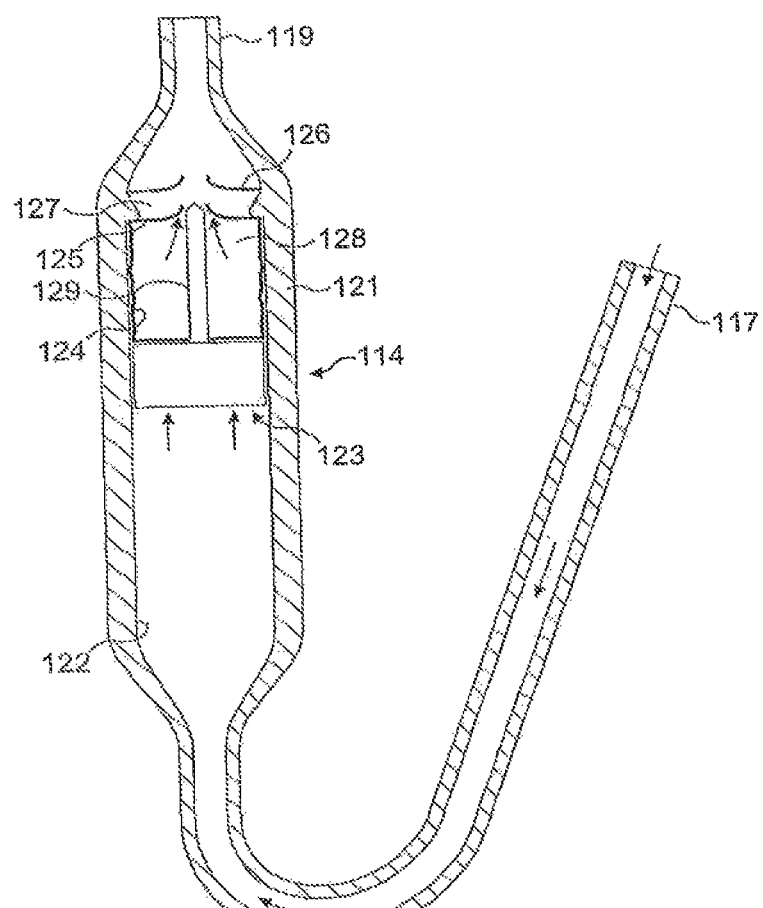
FIG. 16 illustrates a sectional view of the delivery device of FIG. 14, where in a second operative state in which the second rupturable membrane is ruptured by the developed pressure.
Figure 17:
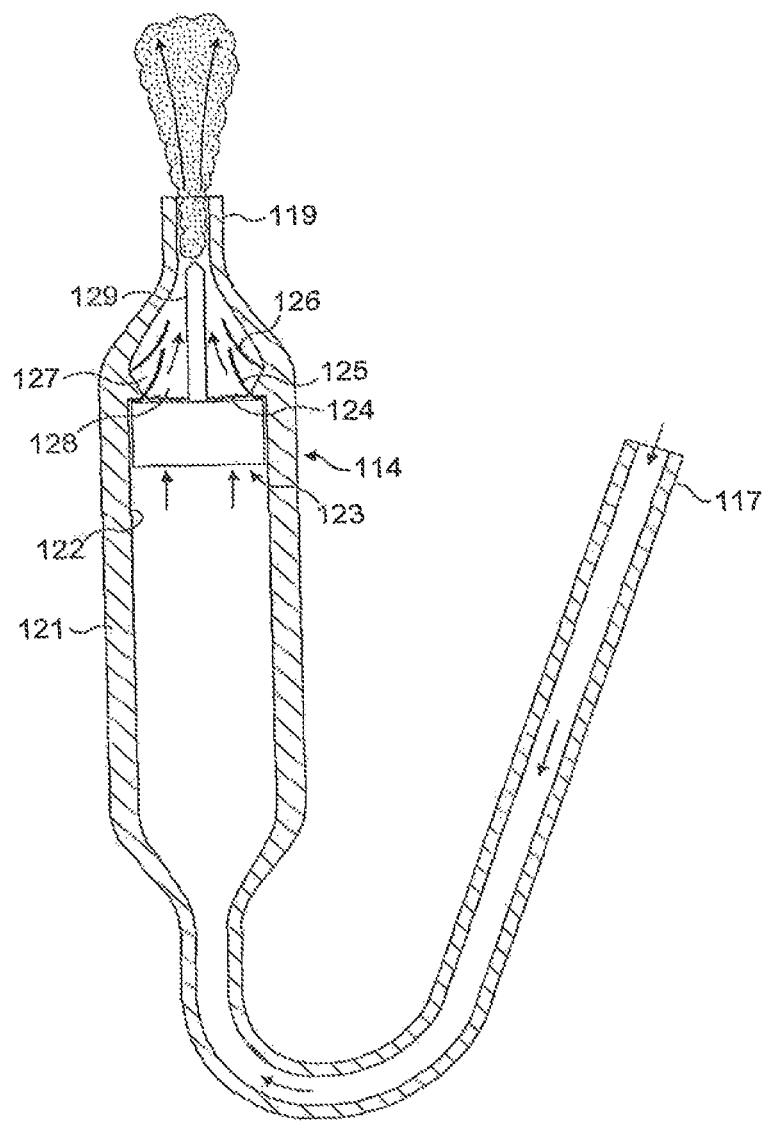
FIG. 17 illustrates a sectional view of the delivery device of FIG. 14, where in a third operative state in which a gas flow entraining powdered substance is delivered by the delivery device.

As illustrated in FIG. 16, the delivery of the gas flow into the chamber 127 ruptures the second rupturable membrane 126, and, as illustrated in FIG. 17, the gas flow entraining the powdered substance is delivered through the nosepiece 119 and into the nasal airway of the user.

In one alternative embodiment the rupturing element 129 could instead be disposed on the body unit 114, such that the first rupturable membrane 125 is biased against the rupturing element 129 and ruptured at a predetermined pressure.

In another alternative embodiment the rupturing element 129 could be omitted from the piston member 123 and the first rupturable membrane 125 of the compressible member 124 could be configured to be ruptured at a predetermined pressure.

In one embodiment the gas flow is at such a pressure and flow as to provide for flow around the posterior margin of the nasal septum and out of the other nostril of the user, in the manner as described in the applicant's earlier WO-A-2000/051672, the content of which is incorporated herein by reference.

FIGS. 18 to 20 illustrate a delivery device in accordance with a sixth embodiment of the present invention.

The delivery device comprises a body unit 214, which is typically gripped in the hand of a user, a mouthpiece 217 through which the user exhales, and a nosepiece 219 for fitting to a nostril of the user and through which substance, in this embodiment particulate substance, here a powdered substance, is delivered to the nasal airway of the user.

In this embodiment the mouthpiece 217 and the nosepiece 219 are integrally formed with the body unit 214, but in other embodiments the mouthpiece 217 and the nosepiece 219 could be formed separately of the body unit 214.

The body unit 214 comprises a housing 221 which includes a first, piston cavity 222, one, rear and of which is fluidly connected to the mouthpiece 217, a second, substance-containing cavity 224 which contains a metered amount of powdered substance and is fluidly connectable to the nosepiece 219, and a by-pass channel 225 which fluidly connects the piston cavity 222 at a location along the length thereof to the cavity 224, a piston member 227 which is slideably disposed, in this embodiment in sealing engagement, within the piston cavity 222, and a rupturable membrane 229 which is disposed at one, forward end of the cavity 224 and normally fluidly separates the nosepiece 219 from the cavity 224.

The piston member 227 includes a rupturing element 231 at a forward surface thereof, and is slideably disposed in the piston cavity 222 in the housing 221 under the bias of the pressure as generated with exhalation by the user into the mouthpiece 217, such that, on exhalation by the user, the piston member 227 is driven forwardly, and, on displacement of the piston member 227 by a predetermined distance, which corresponds to a configuration in which the piston member 227 is located forwardly of the inlet opening to the by-pass channel 225 and the mouthpiece 217 is in fluid communication with the by-pass channel 225, and hence the cavity 224, the membrane 229 is ruptured, which provides for delivery of an exhalation air flow through the cavity 224, which entrains the powdered substance therein, and from the nosepiece 219.

Operation of the above-described delivery device will now be described hereinbelow with particular reference to FIGS. 19 and 20 of the accompanying drawings.

The user first inserts the nosepiece 219 into one of his or her nostrils and grips the mouthpiece 217 in his or her mouth.

The user then exhales through the mouthpiece 217, which provides for the piston member 227 to be driven forwardly under the generated pressure.

As illustrated in FIG. 19, on displacement of the piston member 227 by a predetermined distance, which corresponds to a configuration in which the piston member 227 is located forwardly of the inlet opening to the by-pass channel 225 and the mouthpiece 217 is in fluid communication with the by-pass channel 225, and hence the cavity 224, the rupturable membrane 229 is ruptured by the rupturing element 231 of the piston member 227.

As illustrated in FIG. 20, on rupturing the rupturable membrane 229, the exhalation breath of the user is delivered as an air flow through the cavity 224, which entrains the powdered substance therein, and delivers the same through the nosepiece 219 and into the nasal airway of the user.

With this configuration, as compared to the delivery device of the above-described second embodiment, an air flow is sustained through the nasal airway subsequent to entrainment of the powdered substance.

In one alternative embodiment the rupturing element 231 could be omitted from the piston member 227 and the rupturable membrane 229 could be configured to be ruptured at a predetermined pressure, which is encountered when the piston member 227 passes beyond the location of the inlet opening to the by-pass channel 225 and the mouthpiece 217 is fluidly connected to the cavity 224.

In one embodiment the air flow is at such a pressure and flow as to provide for flow around the posterior margin of the nasal septum and out of the other nostril of the user, in the manner as described in the applicant's earlier WO-A-2000/051672, the content of which is incorporated herein by reference.

FIGS. 21 to 25 illustrate a delivery device in accordance with a seventh embodiment of the present invention.

The delivery device comprises a body unit 314, which is typically gripped in the hand of a user, a substance-supply unit 315 which is disposed within the body unit 314 and operable to deliver substance, a mouthpiece 317 through which the user exhales, and a nosepiece 319 for fitting to a nostril of the user and through which the substance, in this embodiment a powdered substance, is delivered to the nasal airway of the user. In an alternative embodiment the delivery device could be configured to deliver a liquid, either as a spray or a jet, such as from a delivery pump.

In this embodiment the nosepiece 319 is integrally formed with the body unit 314, but in other embodiments the nosepiece 319 could be formed separately of the body unit 314.

The body unit 314 comprises a housing 321, in this embodiment a tubular section which defines a cavity 322, within which the substance-supply unit 315 is slideably disposed, such that, in a storage configuration, as illustrated in FIG. 21, the mouthpiece 317 extends at least partially into the housing 321 to present a compact device, and, in a normal, operative configuration, the substance-supply unit 315 is retracted within the housing 321 and the mouthpiece 317 drawn outwardly of the housing 321, as illustrated in FIG. 22.

In this embodiment, as illustrated in FIG. 22, the mouthpiece 317 is articulated to the substance-supply unit 315, such as to allow the mouthpiece 317 to be bent relative to the nosepiece 319, such as to enclose an acute angle with the nosepiece 319 and thereby enable the mouthpiece 317 and the nosepiece 319 to be fitted simultaneously into respective ones of the mouth and a nostril of a subject.

In this embodiment, as illustrated in FIG. 24, the substance-supply unit 315 and the mouthpiece 317 are configured such that the mouthpiece 317 can alternatively act as a plunger to deliver the substance as contained by the substance-supply unit 315 where the subject is unable to generate an exhalation air flow, such as where the subject is unconscious or uncooperative.

One, normal mode of operation of the above-described delivery device will now be described hereinbelow with particular reference to FIGS. 22 and 23 of the accompanying drawings.

The user first withdraws the mouthpiece 317, which acts to withdraw the substance-supply unit 315 along the cavity 322 in the housing 321, until the substance-supply unit 315 is latched in an operative position, and then bends the articulated mouthpiece 317 relative to the nosepiece 319, such as to provide an operative configuration.

The user then inserts the nosepiece 319 into one of his or her nostrils and grips the mouthpiece 317 in his or her mouth.

The user then exhales through the mouthpiece 317, which actuates the substance-supply unit 315, in this embodiment by entraining a powdered substance from a ruptured chamber in the exhalation breath of the subject.

In another embodiment the substance-supply unit 315 could comprise a breath-operated delivery mechanism, which is primed, typically by loading a biasing element, and actuated in response to detection of an exhalation air flow as generated with exhalation by the subject.

In one embodiment the gas flow is at such a pressure and flow as to provide for flow around the posterior margin of the nasal septum and out of the other nostril of the user, in the manner as described in the applicant's earlier WO-A-2000/051672, the content of which is incorporated herein by reference.

Another mode of operation of the above-described delivery device will now be described hereinbelow with particular reference to FIGS. 24 and 25 of the accompanying drawings.

The user first withdraws the mouthpiece 317, which acts to withdraw the substance-supply unit 315 along the cavity 322 in the housing 321, until the substance-supply unit 315 is latched in an operative position.

The nosepiece 319 is then inserted into one of the nostrils of the subject and the mouthpiece 317 used as a plunger to deliver the substance as contained by the substance-supply unit 315 from the nosepiece 319 and into the nasal cavity of the subject.

In this embodiment the mouthpiece 317 collapses to compress gas as contained therein, with a finger or thumb of the user occluding the inlet opening to the mouthpiece 317, thereby generating an air flow which entrains powdered substance from a ruptured chamber in the substance-supply unit 315.

In another embodiment the substance-supply unit 315 could comprise a flow-operated delivery mechanism, which is primed, typically by loading a biasing element, and actuated in response to detection of an airs w as generated by collapse of the mouthpiece 317.

Finally, it will be understood that the present invention has been described in its preferred embodiments and can be modified in many different ways without departing from the scope of the invention as defined by the appended claims.

For example, in the above-described second to sixth embodiments, the rupturing element 129, 231 could instead be formed with or attached to a substance-containing capsule, such as a blister.

In another modification, in the above-described second to sixth embodiments, the rupturing element 129, 231 could be omitted and the rupturable membranes 125, 126, 229 could be formed as pressure-sensitive valves, which are opened on the generation of predetermined pressures.

The invention claimed is:

1. A delivery device for delivering a metered amount of a substance, the delivery device comprising:
   a mouthpiece unit including a mouthpiece through which a user can in use exhale;
   an outlet unit through which the substance is in use delivered;
   a substance-supply unit which is actuatable to deliver the substance; and
   a body unit in which the substance-supply unit is movably disposed between a storage configuration and an operative configuration;
   wherein the mouthpiece unit is coupled to the substance-supply unit, the substance-supply unit being movable between the storage and operative configurations by movement of the mouthpiece unit;
   wherein the substance-supply unit slides in a substantially linear direction, longitudinally within the body unit from the storage configuration to the operative configuration when the substance-supply unit is moved into the operative configuration; and
   wherein the mouthpiece is articulated to the substance-supply unit and movable relative to the body unit when the substance-supply unit is in the operative configuration.

2. The delivery device of claim 1, wherein the outlet unit is integrally formed with the body unit.

3. The delivery device of claim 1, wherein the body unit comprises a housing which includes a cavity in which the substance-supply unit is slideably disposed.

4. The delivery device of claim 1, wherein:
   the mouthpiece unit is fluidly connected to the substance-supply unit; and
   the substance-supply unit is actuatable in response to exhalation by the user through the mouthpiece.

5. The delivery device of claim 1, wherein the substance-supply unit is actuatable in response to movement of the mouthpiece.

6. The delivery device of claim 1, wherein the outlet unit is a nosepiece and the delivery device is a nasal delivery device for delivering the substance to a nasal airway of the user.

7. The delivery device of claim 1, wherein the substance is a particulate substance.

8. The delivery device of claim 1, wherein the substance is a powdered substance.

9. The delivery device of claim 1, wherein the substance is a liquid substance.

* * * * *